(12) United States Patent
Qin et al.

(10) Patent No.: US 12,338,457 B2
(45) Date of Patent: Jun. 24, 2025

(54) BIOLOGICALLY FUNCTIONAL SOFT TISSUE SCAFFOLDS AND IMPLANTS

(71) Applicant: LifeNet Health, Virginia Beach, VA (US)

(72) Inventors: Xiaofei Qin, Virginia Beach, VA (US); Silvia Chen, Virginia Beach, VA (US)

(73) Assignee: LifeNet Health, Virginia Beach, VA (US)

( * ) Notice: Subject to any disclaimer, the term of this patent is extended or adjusted under 35 U.S.C. 154(b) by 61 days.

(21) Appl. No.: 17/871,149

(22) Filed: Jul. 22, 2022

(65) Prior Publication Data

US 2022/0372438 A1    Nov. 24, 2022

Related U.S. Application Data

(63) Continuation of application No. 15/549,771, filed as application No. PCT/US2016/017168 on Feb. 9, 2016, now Pat. No. 11,434,469.

(60) Provisional application No. 62/114,528, filed on Feb. 10, 2015.

(51) Int. Cl.
| | |
|---|---|
| A61L 27/36 | (2006.01) |
| A61F 2/02 | (2006.01) |
| A61L 27/56 | (2006.01) |
| C12N 5/00 | (2006.01) |

(52) U.S. Cl.
CPC ............ *C12N 5/0068* (2013.01); *A61F 2/02* (2013.01); *A61L 27/3604* (2013.01); *A61L 27/3687* (2013.01); *A61L 27/3691* (2013.01); *A61L 27/56* (2013.01); *A61L 2400/06* (2013.01); *C12N 2533/90* (2013.01)

(58) Field of Classification Search
None
See application file for complete search history.

(56) References Cited

U.S. PATENT DOCUMENTS

| | | |
|---|---|---|
| 5,869,080 A | 2/1999 | McGregor et al. |
| 5,948,429 A | 9/1999 | Bell et al. |
| 6,293,970 B1 | 9/2001 | Wolfinbarger et al. |
| 6,544,289 B2 | 4/2003 | Wolfinbarger et al. |
| 6,569,200 B2 | 5/2003 | Wolfinbarger et al. |
| 6,649,162 B1 | 11/2003 | Biering et al. |
| 6,734,018 B2 | 5/2004 | Wolfinbarger et al. |
| 6,743,574 B1 | 6/2004 | Wolfinbarger et al. |
| 7,063,726 B2 | 6/2006 | Crouch et al. |
| 7,338,757 B2 | 3/2008 | Wolfinbarger et al. |
| 7,498,040 B2 | 3/2009 | Masinaei et al. |
| 7,498,041 B2 | 3/2009 | Masinaei et al. |
| 8,357,402 B2 | 1/2013 | Ingram et al. |
| 8,563,232 B2 | 10/2013 | Wolfinbarger et al. |
| 8,574,826 B2 | 11/2013 | Wolfinbarger et al. |
| 2010/0030340 A1 | 2/2010 | Wolfinbarger et al. |
| 2010/0036503 A1 | 2/2010 | Chen et al. |
| 2010/0040687 A1 | 2/2010 | Pedrozo et al. |
| 2011/0015757 A1 | 1/2011 | Wolfinbarger et al. |
| 2011/0045044 A1 | 2/2011 | Masinaei et al. |
| 2011/0262515 A1 | 10/2011 | Lauritzen et al. |
| 2011/0262541 A1 | 10/2011 | Lauritzen et al. |
| 2013/0218294 A1 | 8/2013 | Wolfinbarger et al. |
| 2014/0065238 A1 | 3/2014 | Wolfinbarger et al. |
| 2014/0154663 A1 | 6/2014 | Wolfinbarger et al. |
| 2014/0180437 A1 | 6/2014 | Wolfinbarger et al. |
| 2014/0221615 A1 | 8/2014 | Nakada et al. |
| 2015/0004638 A1 | 1/2015 | Goerne et al. |

FOREIGN PATENT DOCUMENTS

| | | |
|---|---|---|
| WO | 9615818 A1 | 5/1996 |
| WO | 2014130953 A1 | 8/2014 |

OTHER PUBLICATIONS

Donovan et al., Nature, Nov. 2001, vol. 414, pp. 92-97.
European Communication Pursuant to Article 94(3) for European Application No. 16 749 720.5, dated Apr. 21, 2020, 6 pages, 2020.
Extended European Search Report for European Application No. 16 749 720.5, dated Sep. 18, 2018, 9 pages 2018.
International Preliminary Report on Patentability for International Application No. PCT/US2016/017168, dated Aug. 15, 2017, 8 pages.
International Search Report for International Application No. PCT/US2017/017168, dated May 2, 2016, 1 page.
Moore et al., Cell Tissue Bank, 2015, 16, pp. 249-259.
Entire patent prosecution history of U.S. Appl. No. 15/549,771, filed Aug. 9, 2017, entitled, "Biologically Functional Soft Tissue Scaffolds and Implants."
Korean Request for the Submission of an Opinion for Korean Application No. 10-2017-7025427, dated Apr. 28, 2023 with translation, 16 pages.

*Primary Examiner* — Teresa E Knight
(74) *Attorney, Agent, or Firm* — Matney Legal Group PLLC

(57) ABSTRACT

The invention relates to biologically functional scaffolds having a porous structure, methods of preparing, and methods of use thereof. The invention also relates to methods of repairing a defect, methods of culturing cells and promoting differentiation of stem cells using the same.

23 Claims, 19 Drawing Sheets

BIOLOGICALLY FUNCTIONAL SOFT TISSUE SCAFFOLDS AND IMPLANTS

This application is a continuation of U.S. application Ser. No. 15/549,771, filed Aug. 9, 2017, which is a U.S. national phase application of International Application No. PCT/US2016/017168, filed Feb. 9, 2016, claiming the benefit of U.S. Provisional Application No. 62/114,528, filed 10 Feb. 2015, the contents of each of which are incorporated herein by their entireties for all purposes.

BACKGROUND OF THE INVENTION

The invention relates to biologically functional scaffolds having a porous structure, methods of preparing, and methods of use thereof. The invention also relates to methods of repairing a defect, methods of culturing cells and promoting differentiation of stem cells using the same.

SUMMARY OF THE INVENTION

The invention relates to methods of preparing a biologically functional scaffold having a porous structure comprising dispersing one or more soft tissue(s) at a temperature between about 0-50° C. to produce a dispersed soft tissue. In one embodiment, the dispersed soft tissue may exclude non-naturally occurring crosslinker or carrier. Two or more types of dispersed soft tissue may be mixed after dispersing. The methods may further comprise freezing, drying or freeze-drying said dispersed soft tissue to produce a biologically functional scaffold.

The invention also relates to biologically functional scaffolds prepared by the methods described herein.

The invention further relates to methods of repairing various defects in a tissue comprising implanting the biologically functional scaffold described herein at the site of defect. Two or more types of dispersed soft tissue may be mixed and applied to a defect. The invention also relates to methods of seeding cells, culturing cells, and promoting differentiation of stem cells using the biologically functional scaffold described herein.

BRIEF DESCRIPTION OF THE DRAWINGS

FIG. 16 illustrates the fibers and fiber bundles in dispersed dermis with a blue dye.

DETAILED DESCRIPTION OF THE INVENTION

In one aspect, the invention relates to methods of preparing a biologically functional scaffold and/or implant having a porous structure. The scaffold described herein may include an implant, which is a scaffold configured to be implanted in vivo. The porous structure may include porous sponge-like structure. The term "porous sponge-like structure" refers to a three-dimensional structure that is porous, elastic, flexible, fibrous, and resilient. In addition, the preferred "porous sponge-like structure" is substantially coherent (or cohesive) in the sense of holding together or staying substantially intact. As used herein, the terms "coherent" or "cohesive" refer to the property that the elements of the structure of a material are maintained substantially intact (in the sense of holding together rather than becoming disassembled or separated). In a dry state, the porous sponge-like scaffold of the present invention may quickly absorb fluid. In the wet state, the porous sponge-like scaffold of the present invention may maintain the porosity, cohesiveness, and/or integrity. The wet porous sponge-like structure may resist certain tensile stress, and bounce back and reabsorb fluid after being released from compression. The porous sponge-like scaffold and/or the biologically functional scaffold may be twisted, folded, rolled, molded, placed and/or inserted into or on the defect such as skin lesion, topical wound, ulcer, breast after lumpectomy or mastectomy, deep or tunneling wound, fistula, or wrapped around the defect of bone, cartilage or soft tissue.

Figure 15:
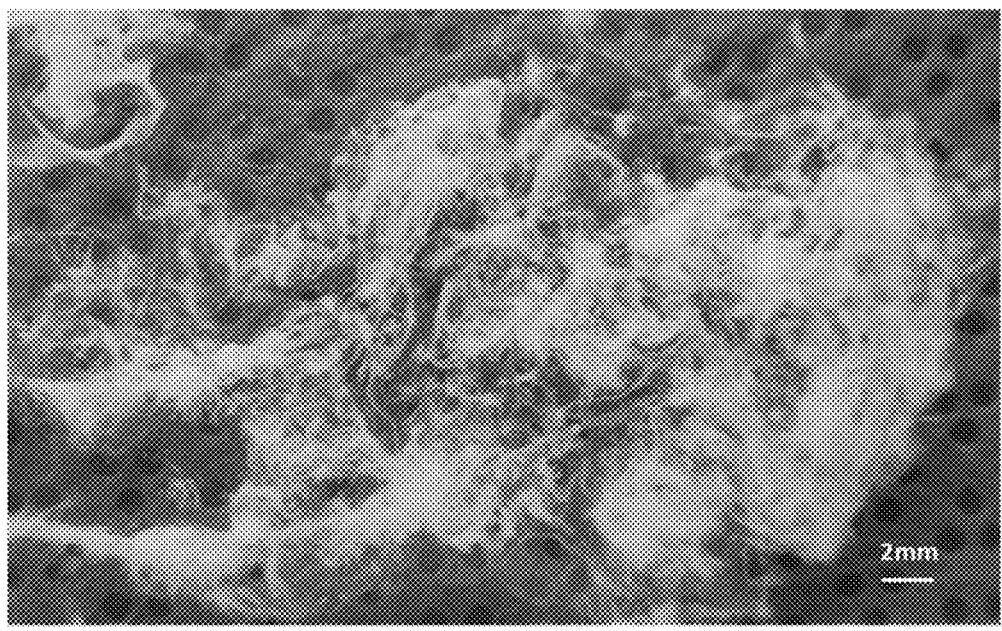
FIGS. 15 and 16 illustrate the dispersed dermis.
Figure 16:
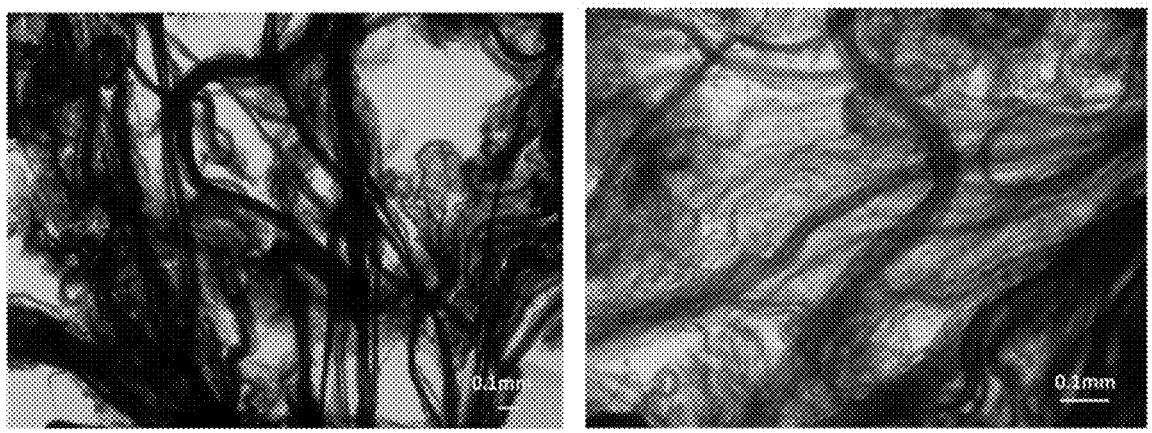

In preferred embodiments of the present invention, the methods described herein may comprise dispersing one or more soft tissue(s) at a temperature between about 0-50° C. to produce a dispersed soft tissue. The dispersing may include loosening the network of extracellular materials in the soft tissue. In some embodiments, the dispersed soft tissue described herein may include a network of fibers as shown in FIGS. 15 and 16. Compared to the native soft tissues, the dispersed soft tissues may have more space among (and/or in between) the extracellular materials and an increased void volume, and the fibers or fiber bundles may be randomly interwoven or intertwined by the dispersion process The native soft tissue is a tissue that connects, supports, and/or surrounds other body structures. In some embodiments, the native soft tissue may be selected from a part or whole organ, (e.g. liver, kidney, pancreases, heart, spleen, and lung), muscle, fat, blood vessel, nerve, tendon, ligament, lining of joints, skin, dermis, pericardium, endocardium, mucosal tissue, fascia, arteries or veins, dura mata, periosteum, amniotic membrane, placental membrane, chorionic membrane, umbilical cord, bladder, small or large intestine, urethra, and/or placenta.

In additional embodiments, the soft tissue described herein is an autograft, an allograft, or a xenograft. In further embodiments, the soft tissue may be a connective tissue excluding cartilage and bone, referring to ectodermally, mesodermally or endodermally derived tissue that may be more or less specialized, and that may be, at least in part, made up of fibers. Most of the connective tissues contemplated in the present invention are less specialized tissues that are rich in extracellular matrix (i.e., collagen, proteoglycan, elastin, hyaluronic acid, fibronectin, laminin, among others), and that surround other more highly ordered tissues and organs. A relatively more specialized tissue contemplated in the present invention is dermis. Varieties of connective tissue that may be used in the present invention include but are not limited to adipose; loose connective tissue; dense, regular, irregular, or elastic connective tissue; and white fibrous connective tissue. The cartilage, however, is not included in the soft tissue herein. Connective tissue may be classified according to concentration of fibers as loose (areolar) and dense, the latter having more abundant fibers than the former. Examples of additional types of fascia that may be used in some embodiments of the present invention include: fascia lata, fascia adherens, fascia brachii, fascia axillaris, antebrachial fascia, abdominal fascia, internal fascia, fascia iliaca, fascia profunda, clavipectoral fascia, fascia cribosa, crucial fascia, deltoid fascia, dorsal deep fascia, pelvic fascia, fascia cruris, lumbar fascia, and pectoral fascia, among others. For practical reasons of availability during procurement and amount of fascia available, fascia lata from the anterior portion of the upper leg may be used in certain embodiments. Connective tissues may be obtained from vertebrates. Connective tissues may also be the product of biotechnological methods, for example, tissue engineered connective tissues produced using cell culture methods, and such a product of biotechnological methods may be included as the soft tissue described herein. In some embodiments, the soft tissues herein may have human, non-human animal, bovine, equine, porcine, ovine, caprine, or piscine origins, among others.

Specific examples of connective tissues that may be used in certain embodiments of the present invention include but are not limited by at least, fascia, dermis, tendons, ligaments, pericardium, urethra, small intestine, muscle, or skin. Examples of different types of fascia that may be used in certain embodiments of the present invention include: fascia lata, fascia adherens, fascia brachii, fascia axillaris, antebrachial fascia, abdominal fascia, internal fascia, fascia iliaca, fascia profunda, clavipectoral fascia, fascia cribosa, crucial fascia, deltoid fascia, dorsal deep fascia, pelvic fascia, fascia cruris, lumbar fascia, and pectoral fascia, among others.

In another aspect, the dispersed soft tissue described herein may or may not optionally include "crudely fragmented connective tissue," referring to connective tissue that has been sliced, ground, carved, chipped, chopped, minced, cut, dissected, rent, ripped, sectioned, snipped, diced, shaved, comminuted, or trimmed into fragments.

Such fragmented connective tissue may have an average diameter greater than about 50 microns and less than about 0.5 cm, for example, having cut dimensions of approximately 0.5×0.5 cm, and a thickness appropriate to the tissue being crudely fragmented. In some embodiments, the crude fragments may not be of uniform size. In one aspect, the dispersed soft tissue described herein may or may not include "homogenized connective tissue" or "connective tissue homogenate" containing connective tissue that has been reduced to particles that are uniformly small and evenly distributed. Homogenized connective tissue may optionally include at least one of water, aqueous solutions, or water miscible polar organic solvents, in addition to the particles. The homogenized connective tissues used in methods of the present invention include particles having an average diameter of less than about 50 microns. In some embodiments, the homogenized connective tissue may be prepared by shear-induced shredding of a composition comprising connective tissue, and optionally, at least one of water, an aqueous solution and a water miscible polar organic solvent.

In another aspect, the dispersed soft tissue and/or the biologically functional scaffold and/or implant may include two, three, four, five, six, seven, eight or more soft tissues described herein. For example, the dispersed soft tissue and/or the biologically functional scaffold and/or implant may include a combination of (i) dermis or fascia and (ii) placental tissues, adipose tissues, tendon ligament tissues, or nerve tissue. In some embodiments, the weight ratio of (i) dermis or fascia to (ii) placental tissues, adipose tissues, tendon ligament tissues, or nerve tissue is about 0.1, 0.2, 0.3, 0.4, 0.5, 0.6, 0.7, 0.8, 0.9, 1, 2, 3, 4, 5, 6, 7, 8, 9 or 10. For another example, the dispersed soft tissue and/or the biologically functional scaffold and/or implant may include a combination of (i) amniotic membrane and (ii) chorionic membrane. In some embodiments, the weight ratio of (i) amniotic membrane to (ii) chorionic membrane is about 0.1, 0.2, 0.3, 0.4, 0.5, 0.6, 0.7, 0.8, 0.9, 1, 2, 3, 4, 5, 6, 7, 8, 9 or 10, with a preferred weight ratio range of 0.1-10, more preferably a range of 0.5-5, or more preferably a range of 0.7-3. In some embodiments, the different types of soft tissue may be layered, for example, a layer of dispersed soft tissue made with amniotic membrane on top of a layer of dispersed soft tissue made with chorionic membrane, or a layer of dispersed soft tissue made with chorionic membrane sandwiched in two layers of dispersed soft tissue made with amniotic membrane. In other embodiments, the dispersed soft tissue and/or the biologically functional scaffold and/or implant may include a combination of soft tissues from different sources, such as human, non-human animal, bovine, equine, porcine, ovine, caprine, or piscine origins, among others.

The method described herein may include adding one or more additional soft tissue to the dispersed soft tissue and/or the biologically functional scaffold and/or implant described herein. Such an added step (of adding one or more additional soft tissue) may be performed before or after dispersing the additional soft tissue.

In another aspect, the soft tissue may be dispersed at a temperature above about −80, −70, −60, −50, −40, −30, −20, −10, −5, 0, 5, 10, 15, 16, 17, 18, 19, 20, 21, 22, 23, 24, 25, 26, 27, 28, 29, 30, 31, 32, 33, 34, 35, 36 or 37° C. In some embodiments, the soft tissue may be dispersed at a temperature below about −70, −60, −50, −40, −30, −20, −10, −5, 0, 5, 10, 15, 16, 17, 18, 19, 20, 21, 22, 23, 24, 25, 26, 27, 28, 29, 30, 31, 32, 34, 35, 36, 37, 38 or 39° C. In additional embodiments, the soft tissue may be dispersed at a temperature of about −80, −70, −60, −50, −40, −30, −20, −10, −5, 0, 5, 10, 15, 16, 17, 18, 19, 20, 21, 22, 23, 24, 25, 26, 27, 28, 29, 30, 31, 32, 33, 34, 35, 36, or 37° C. In further embodiments, the soft tissue may be dispersed at a temperature between about −80 and about 50° C., −20 and about 50° C., −10 and about 50° C., about −5 and about 50° C., about 0 and about 50° C., about 0 and about 37° C., about 5 and about 24° C., about 10 and about 24° C., about 15 and about 24° C., about −5 and about 10° C., about −5 and about 15° C., or about 0 and about 15° C. In another aspect, the soft tissue may be dispersed mechanically by chopping, skiving, miffing, grinding, slicing and/or beating the soft tissue (e.g. by a blender, a beater, and a mixer). In some embodiments, the temperature of the soft tissue may rise above ambient temperature due to the dispersing process, but no additional heat is applied to the soft tissue. In a preferred embodiment, the temperature of soft tissue may be controlled by adding, e.g., cold solution (e.g., water and saline) or ice (e.g., made from water or isotonic solution) to the soft tissue prior to, or during, the dispersing process. In another embodiment, the method may exclude treating the soft tissue with heat above about 24, 25, 26, 27, 28, 29, 30, 31, 32, 33, 35, 36, 37, 38, 40, 45, 50, 60, 70, 80, 90, 100, 150, or 200° C. prior to, during and/or after the dispersing. In some embodiments, the method excludes treating the soft tissue with heat below about 50, 70, 90, or 110° C. prior to, during, and/or after the dispersing. In other embodiments, the method excludes treating the soft tissue with heat between about 26 and about 200° C., about 30 and about 150° C., about 40 and about 120° C., about 50 and about 110° C., and about 50 and about 100° C. prior to, during, and/or after the dispersing. In another aspect, the method may exclude sonication, microwave irradiation, or conventional heat transfer from a heating component, among other methods known in the art.

As used herein, the term "about" modifying, for example, the quantity of an ingredient in a composition, concentrations, volumes, process temperature, process time, yields, flow rates, pressures, and like values, and ranges thereof, refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods; and like considerations. The term "about" also encompasses amounts that differ due to aging of, for example, a composition, formulation, or cell culture with a particular initial concentration or mixture, and amounts that differ due to mixing or processing a composition or formulation with a particular initial concentration or mixture. Whether modified by the term "about" the claims appended hereto include equivalents to these quantities. The term "about" further may refer to a range of values that are similar to the stated reference value. In certain embodiments, the term "about" refers to a range of values that fall within 10, 9, 8, 7, 6, 5, 4, 3, 2, 1 percent or less of the stated reference value.

In some embodiments, the one or more soft tissue(s) described herein is dispersed for about 5 seconds, 10 seconds, 15 seconds, 20 seconds, 25 seconds, 30 seconds, 40 seconds, 50 seconds, 60 seconds, 2 minutes, 3 minutes, 4 minutes, 5 minutes, 10 minutes, 15 minutes, 30 minutes, 60 minutes, 2 hours, 5 hours, 10 hours, 24 hours, 48 hours or 72 hours or more. In additional embodiments, the one or more soft tissue(s) described herein is dispersed for about 20 seconds, 30 seconds, 60 seconds, 2 minutes, 3 minutes, 4 minutes, 5 minutes, 10 minutes, 15 minutes, 30 minutes, 60 minutes, 2 hours, 5 hours, 10 hours, 24 hours, 48 hours or 72 hours or less. In further embodiments, the one or more soft tissue(s) described herein is dispersed for between about 20 seconds and 72 hours, about 30 seconds and 30 minutes, about 30 seconds and 20 minutes, about 30 seconds and 10 minutes, preferably between about 1 minute and 20 minutes, between about 1 minute to 10 minutes, or between about 1 minute to 6 minutes.

In some embodiments, the one or more soft tissue(s) is dispersed in the presence of a solution or solvent (e.g. water, and saline solution). The solution or solvent may be in the form of liquid or solid. In additional embodiments, the one or more soft tissue(s) is dispersed in the presence of a solid (e.g. ice formed from water, and solid formed from saline solution). The solid may comprise one or more salt granulate and/or one or more sugar granulate. The salt granulate may for example comprise $NaCl_2$ and/or $CaCl_2$, and the sugar granulate may for example comprise glucose, sucrose, and/or fructose. In another embodiment, the solid may have the size of about 0.5 $mm^3$, 1 $mm^3$, 2 $mm^3$, 4 $mm^3$, 10 $mm^3$, 2 $cm^3$, 4 $cm^3$, 6 $cm^3$, 8 $cm^3$, 10 $cm^3$, or above. In additional embodiments, the size of a solid may be between about 0.5 $mm^3$ and 20 $cm^3$, between about 1 $mm^3$ and 20 $cm^3$, between about 5 $mm^3$ and 20 $cm^3$, between about 1 $cm^3$ and 20 $cm^3$, or between about 1 $cm^3$ and 10 $cm^3$. In further embodiments, the method described herein may further comprise dissolving the solid during and/or after dispersing the soft tissue(s). In yet additional embodiments, a weight ratio of the one or more moist soft tissue(s) to solution or solvent in the dispersed soft tissue (in other words, the wet weight of tissue to the solution) is about 0.01, 0.05, 0.1, 0.2, 0.3, 0.4, 0.5, 0.6, 0.7, 0.8, 0.9 or 1.0 or more. The weight ratio of the dispersed one or more soft tissue(s) to solution or solvent in the dispersed soft tissue may also be about 0.02, 0.05, 0.1, 0.2, 0.3, 0.4, 0.5, 0.6, 0.7, 0.8, 0.9 or 1.0 or less. Further, the weight ratio of one or more soft tissue(s) to solution or solvent in the dispersed soft tissue may be from about 0.010 to 10.0, preferably from about 0.02 to 2.0, more preferably from about 0.04 to 1.0, from about 0.05 to 1.5, from about 0.05 to 1.0, or from about 0.1 to 1.0.

In some embodiments, the weight percentage of said one or more soft tissue(s) in said dispersed soft tissue is about 2, 5, 10, 15, 20, 30, 40, 50, 60, 70, 80, 90, 92, 94, 96, 98, 100% or more in a dry state. In additional embodiments, the weight percentage of said one or more soft tissue(s) in said dispersed soft tissue is about 3, 5, 10, 15, 20, 30, 40, 50, 60, 70, 80, 90, 91, 93, 95, 97, 99, 100% or less in a dry state. In further embodiments, the weight percentage of said one or more soft tissue(s) in said dispersed soft tissue is from about 2% to about 100%, preferably from about 50% to about 90%, from about 50% to about 80%, from 60% to 100%, from 80% to about 100%, or from about 60% to about 100% in a dry state.

In some embodiments, the weight percentage of said dispersed soft tissue in the biologically functional scaffold and/or implant is about 50, 60, 70, 80, or 90% or more in a dry state. In additional embodiments, the weight percentage of said dispersed soft tissue in said biologically functional scaffold and/or implant is about 50, 60, 70, 80, or 90%, or 100% or less in a dry state. In further embodiments, the weight percentage of said dispersed soft tissue in said biologically functional scaffold and/or implant is from about 50% to about 100%, from about 70% to about 100%, from about 80% to about 100%, or from about 90% to about 100% in a dry state. The amount of dispersed soft tissue in a biologically functional scaffold and/or implant may be varied to adjust the density, porosity, and/or viscosity characteristics of the biologically functional scaffold and/or implant as well as the re-hydration characteristics of the porous structure. Moreover, incorporating additional dispersed soft tissue in the biologically functional scaffold and/or implant may strengthen the three-dimensional framework and increase the integrity of the porous structure. Incorporating more dispersed soft tissue in the biologically functional scaffold and/or implant also may decrease or increase the cellular response towards the framework of the porous structure by facilitating cellular attachment, migration, and/or proliferation.

In one embodiment, the dispersed soft tissue of the present invention does not require, and thus in a preferred embodiment does not comprise, an additional crosslinker or carrier in addition to natural (i.e., endogenous) crosslinker(s) and natural carrier(s) from the one or more soft tissue(s). Thus, in a preferred embodiment, the methods and resulting products of the present invention may consist essentially of (and/or consist of) natural crosslinker(s) and natural carrier(s) from the one or more soft tissue(s). In another embodiment, however, the methods and resulting products may optionally include the addition of additional crosslinker(s) or carrier(s) in addition to the natural crosslinker(s) and natural carrier(s) from the one or more soft tissue(s) after dispersing the soft tissue, and, accordingly, the biologically functional scaffold and/or implant in this embodiment may optionally comprise such additional non-natural crosslinker(s) or carrier(s) as described below.

With regard to naturally occurring crosslinkers and carriers, the soft tissue described herein may comprise a naturally occurring crosslinker that is a physical and/or chemical bond at least between two parts of the soft tissue. The chemical bonds may include ionic, covalent, non-covalent, and/or metallic bonds. Furthermore, as indicated above, in some preferred embodiments, the methods described herein do not include crosslinking the one or more soft tissue(s) and/or the dispersed soft tissue by non-naturally occurring bonds using non-naturally occurring crosslinkers.

With specific regard to non-naturally occurring crosslinkers or carriers, in some embodiments, as indicated above, the dispersed soft tissue and/or biologically functional scaffold described herein may optionally include the addition of a non-naturally occurring crosslinkers, also referred to herein as crosslinking agents, in addition to the natural crosslinker(s) and natural carrier(s) from the one or more soft tissue(s) after dispersing the soft tissue, wherein the optionally added non-naturally occurring crosslinker can be selected from the group consisting of propylene glycol alginate, glycerol, sucrose octasulfate, polyethylene glycol, polymethylmethacrylate, polyurethane, acryloilmorpholine, N,N-dimethyl acrylamide, N-vinyl pyrrolidone and tetrahydrofurfuryl methacrylate, hydroxyapatite, polyurethane, and polylactic acid, glutaraldehyde, glyceraldehyde, poly(ethylene glycol) diepoxide crosslinker, poly(ethylene glycol) diglycidyl ether, EDC and NHS, transglutaminase, ethylenediamine, lysyl oxidase family, hexamethylene diisocyanate (HMDIC), dimethyl suberimidate (DMS), dimethyl-3-3'-dithiobispropionimidate (DTBP), and acryl azide, and/or combinations thereof. In additional embodiments, the dispersed soft tissue and/or biologically functional scaffold described herein may optionally include a photoactive agent selected from the group consisting of a xanthene dye, naphthalimide compounds, riboflavin-5-phosphate, N-hydroxypyridine-2-(1H)-thione, N-(20-ethylaminoethyl)-4-amino-1,8-naphthalimide, bis-diazopyruvamide-N,N9-bis (3-diazopyruvoyl)-2,29-(ethylenedioxy)bis-(ethylamine) (DPD), diazopyruvoyl (DAP), methylene blue, erythrosin, phloxime, thionine, methylene green, rose Bengal, acridine orange, xanthine dye, thioxanthine dye, ethyl eosin, and eosin Y, and/or combinations thereof.

In another aspect, the soft tissue described herein may also comprise a natural carrier. The carriers described herein are configured to form a three-dimensional framework to be injected or implanted into wound, defect, and/or surgical sites. The natural carriers are carriers that naturally occur in a soft tissue, and, for example, include extracellular matrices, such as collagen and hyuronic acid or elastin. In some embodiments, the dispersed soft tissue and/or biologically functional scaffold described herein may optionally include a non-naturally occurring carrier selected from the group consisting of gelatin, agarose, modified hyaluronic acid, propylene glycol alginate, polyethylene glycol, glycerol, polymethylmethacrylate, polyurethane, acryloilmorpholine, N,N-dimethyl acrylamide, N-vinyl pyrrolidone and tetrahydrofurfuryl methacrylate, hydroxyapatite, cross-linked or functionalized hyaluronan-based collagen and alginate, polyurethane, and polylactic acid, and/or combinations comprising at least one of the foregoing polymers. In additional potential embodiments, the dispersed soft tissue and/or biologically functional scaffold described herein may optionally include salts of calcium, barium, aluminum, strontium, copper, zinc, magnesium, manganese, cobalt, or iron, glutaraldehyde, glyceraldehyde, poly(ethylene glycol) diepoxide crosslinker, poly(ethylene glycol) diglycidyl ether, EDC and NHS, transglutaminase, ethylenediamine, lysyl oxidase family, hexamethylene diisocyanate (HMDIC); dimethyl suberimidate (DMS), dimethyl-3-3'-dithiobispropionimidate (DTBP), acryl azide, and/or combinations thereof.

As indicated above, in one embodiment the dispersed soft tissue and/or biologically functional scaffold of the present invention does not require, and thus in a preferred embodiment does not comprise, an additional crosslinker in addition to a natural crosslinker(s) from the soft tissue. In another embodiment, however, the dispersed soft tissue described herein may optionally include an additional carrier in addition to a natural carrier(s) from the soft tissue. For example, the dispersed soft tissue in an alternative embodiment may optionally comprise, alginate, propylene glycol alginate, native or crosslinked chitosan, starch, polyethylene glycol, cellulose and its derivatives (such as cellulose acetate, carboxymethyl cellulose, and methyl cellulose), xanthan gum, dextran, hyaluronic acid, chondroitin sulfate, locust bean gum, gum tragacanth, gum arabic, curdlan, pullulan, scleroglucan, lower methoxylpectin, or carrageenan. The dispersed soft tissue may or may not optionally include a carrier solution. If included, the carrier solution may comprise salts of calcium, barium, aluminum, strontium, copper, zinc, magnesium, manganese, cobalt, or iron; glutaraldehyde, glyceraldehyde, genipin, glucose or ribose, poly(ethylene glycol) diepoxide crosslinker, poly(ethylene glycol) diglycidyl ether, EDC and NHS, transglutaminase, ethylenediamine, lysyl oxidase family, hexamethylene diisocyanate (HMDIC); dimethyl suberimidate (DMS), dimethyl-3-3'-dithiobispropionimidate (DTBP), or acryl azide. The optional carrier solution may also comprise natural and/or synthetic polymers such as native or modified collagen, gelatin, agarose, modified hyaluronic acid, fibrin, chitin, biotin, avidin, MATRIGEL®, HUMAN EXTRACELLULAR MATRIX®, proteoglycans, laminin, fibronectin, elastin, heparin, glycerol, polymethylmethacrylate, polyurethane, acryloilmorpholine, N,N-dimethyl acrylamide, N-vinyl pyrrolidone and tetrahydrofurfuryl methacrylate, hydroxyapatite, cross-linkage or functionalization of hyaluronan-based collagen and alginate, polyurethane, polylactic acid, or a combination comprising at least one of the foregoing polymers in addition to a natural carrier(s) from the soft tissue. In additional embodiments, for example, the dispersed soft tissue and/or biologically functional scaffold described herein may or may not include an optional additional carrier in addition to a natural carrier(s) from the soft tissue, wherein the carrier is selected from the group consisting of native collagen, hyaluronic acid, fibrin, chitin, biotin, avidin, MATRIGEL®, HUMAN EXTRACELLULAR MATRIX®, proteoglycans, laminin, fibronectin, elastin, heparin, alginate, genipin, chitosan, starch, glucose or ribose, cellulose and its derivatives (such as cellulose acetate, carboxymethyl cellulose, and methyl cellulose), xanthan gum, dextran, hyaluronic acid, chondroitin sulfate, locust bean gum, gum tragacanth, gum arabic, curdlan, pullulan, scleroglucan, lower methoxyl pectin, and carrageenan, and/or combinations thereof. Moreover, in further embodiments, the dispersed soft tissue and/or biologically functional scaffold described herein may or may not include an optional additional crosslinker in addition to a natural crosslinker(s) from the soft tissue, wherein the optional additional crosslinker is selected from the group consisting of alginate, starch, cellulose and its derivatives (such as cellulose acetate, carboxymethyl cellulose, and methyl cellulose), xanthan gum, dextran, carrageenan, genipin, hyaluronic acid, condroitin sulfate, locust bean gum, gum tragacanth, gum arabic, curdlan, pullulan, scleroglucan, and lower methoxylpectin, glucose or ribose, native collagen, hyaluronic acid, fibrin, chitin, biotin, avidin, MATRIGEL®, HUMAN EXTRACELLULAR MATRIX®, proteoglycans, laminin, fibronectin, elastin, heparin, and chitosan, and/or combinations thereof.

The methods described herein may further comprise freezing, drying, or freeze-drying said dispersed soft tissue to produce a biologically functional scaffold and/or implant. In another embodiment, the freezing and freeze-drying may be conducted at a controlled freezing rate. The controlled freezing rate may be between from about 1° C. to 20° C. per minute, from about 2° C. to 10° C. per minute, from about 3° C. to 10° C. per minute, from about 3° C. to 6° C. per minute. In some embodiments, the functional scaffold and/or implant may be freeze-dried to a point such that the freeze-dried fragments have an average residual moisture of less than about 10, 5, 4, 3, 2, 1, 0.5, or 0.1 wt %. In further embodiments, the functional scaffold and/or implant may be dried, and/or freeze-dried to a point such that the dried or freeze-dried fragments have residual moisture from about 0.01% to 10%, from about 0.01% to 5%, from about 0.01% to 3%, from about 0.1% to 3%, from 0.5% to 3%, or from 1% to 3%.

In another aspect, the dispersed soft tissue described herein consists essentially of and/or consists of the one or more soft tissue(s); and solution or solvent. In some embodiments, the biologically functional scaffold and/or implant consists essentially of and/or consists of components from the one or more soft tissue(s). The term "essentially consisting of" defines the scope of the scaffold and/or implant to include additional elements that do not materially affect the porosity or void fraction of the scaffold and/or implant consisting of initial elements. For example, the dispersed soft tissue consisting essentially of one or more soft tissue(s) may include elements in addition to the one or more soft tissue(s) that do not materially affect the porosity or void fraction of the dispersed soft tissue consisting of the one or more soft tissue(s). Materially affecting the porosity or void fraction herein means changing the porosity or void fraction at least by about 0.5, 1, 2, 3, 4, 5, 7, 9, 10, 12, 15, 20, 25, 30, or 40%.

In some embodiments, the density of said biologically functional scaffold and/or implant is about 0.001 g/cm$^3$, 0.01 g/cm$^3$, 0.05 g/cm$^3$, 0.1 g/cm$^3$, 0.5 g/cm$^3$, 0.7 g/cm$^3$, 0.9 g/cm$^3$ or more in a dry state. In additional embodiments, the density of said biologically functional scaffold and/or implant is about 0.002 g/cm$^3$, 0.02 g/cm$^3$, 0.06 g/cm$^3$, 0.3 g/cm$^3$, 0.6 g/cm$^3$, 0.8 g/cm$^3$, 0.9 g/cm$^3$, 1.0 g/cm$^3$, 1.2 g/cm$^3$, 1.5 g/cm$^3$ or less in a dry state. In further embodiments, the density of said biologically functional scaffold and/or implant is from about 0.01 g/cm$^3$ to about 1 g/cm$^3$, from about 0.01 g/cm$^3$ to about 1 g/cm$^3$, from about 0.02 g/cm$^3$ to about 0.5 g/cm$^3$, from about 0.02 g/cm$^3$ to about 0.2 g/cm$^3$, from about 0.03 g/cm$^3$ to about 0.2 g/cm$^3$ in a dry state.

In some embodiments, the biologically functional scaffold and/or implant comprises pores having an average diameter of about 1, 5, 10, 100, 200, 300, 400, 500, 700, 1000, 1500, 2000, 3000, or 4000 µm or more. In additional embodiments, the biologically functional scaffold and/or implant comprises pores having an average diameter of about 2, 6, 20, 100, 200, 300, 400, 500, 700, 900, 1000, 1300, 1500, 2000, 3000, or 4000 µm or less. In further embodiments, the biologically functional scaffold and/or implant comprise pores having an average diameter from about 1 µm to 4000 µm, from 1 µm to 1000 µm, from about 10 µm to 1000 µm, from about 20 µm to 500 µm, from about 20 µm to 200 µm, from about 50 µm to 200 µm on an average. In some embodiments, the biologically functional scaffold and/or implant has up to 70% of pores with a diameter less than 50 µm. In some embodiments, the biologically functional scaffold and/or implant has more than 30% pores with a diameter from about 50 µm to 200 µm. In some embodiments, the biologically functional scaffold and/or implant comprise more than 50% pores with a diameter from about 20 µm to 200 µm.

In some embodiments, an average void volume of the biologically functional scaffold and/or implant is about 10, 20, 30, 40, 50, 60, 70, 80, 90, 95, 96, 97, 98, 99% or more. In additional embodiments, an average void volume of the biologically functional scaffold and/or implant is about 10, 20, 30, 40, 50, 60, 70, 80, 90, 95, 96, 97, 98, 99% or less. In further embodiments, an average void volume of the biologically functional scaffold and/or implant is from about 10% to about 99%, from about 30% to 99%, from about 50% to about 99%, from about 70% to 99%, from about 80% to about 99%, or from about 80% to 96%. In some embodiments, the average void volume of the biologically functional scaffold is from about 1 cc/ to 30 cc/g, from about 2 cc/g to 20 cc/g, from about 3 cc/g to 20 cc/g, from about 5 cc/g to 20 cc/g. In some embodiments, the average void volume of the biologically functional scaffold can be controlled by adjusting the volume of liquid added to the dispersed soft tissue prior to drying or freeze drying.

In one aspect, the biologically functional scaffold and/or implant comprises fibers and/or sheets. In some embodiments, the biologically functional scaffold and/or implant prepared by the methods described herein may have collagen fiber, collagen fiber bundle dimensions or diameters more similar to its natural state, compared to some other processing techniques in the prior art. In some embodiments, the fibers or fiber bundles in the scaffold are intertwined or randomly interwoven. Previous techniques have led to a tissue fiber with smaller sizes than the natural fibers and thus may degrade faster in vivo. Moreover, the soft tissue in the methods described herein is preferably dispersed without being denatured, micronized, or cryofractured, thus preferably having no change or only minimal change of the extracellular matrix macromolecule components (for example: collagen, proteoglycan, elastin, hyaluronic acid, laminin, fibronectin, among other), and having no change or only minimal change in the relative ratio of macromolecule components in the dispersed soft tissue, and/or the biologically functional scaffold and/or implant. In the other words, the extracellular matrix macromolecules of the resulting biologically functional scaffold are preferably not modified (or at least not substantially modified) by the preferred methods of the present invention. Dispersing the soft tissue according to preferred methods of the present invention may open the structure of the soft tissue to facilitate cell infiltration and/or tissue-in-growth after scaffold implantation, but preferably may not modify the cell-scaffold and/or implant interaction at the micro scale level, unlike implants prepared by other techniques. At the same time, the fiber and/or fiber bundle dimension (e.g. diameter, or width, and length) of preferred scaffolds and/or implants of the present invention may support a framework with opened pore structure and with a network of fibers, fiber bundles and/or sheets that may provide a relatively strong and stable framework without needing additional (non-natural) crosslinking or adding a carrier. In some embodiments, the fiber or fiber bundle dimension may provide a stable framework for the scaffold and/or implant of the present invention without modifying or weakening the integrity and cohesiveness of the scaffold and/or implant. In preferred embodiments, the structure of the scaffold and/or implant of the present invention can stay intact after rehydration and agitation in liquid, and the scaffold and/or implant of the present invention can allow for biocompatible cellular and tissue response and good volume retention after implantation in an animal. The volume retention after implantation in an animal may be measured by the largest cross-section area of the implanted scaffold at different times after implantation. For example, the biologically functional scaffold and/or implant may have recipient's cell infiltration and angiogenesis after 1-4 weeks of implantation, and maintain scaffold and/or implant volume (e.g. the largest cross-section area of implanted scaffold) from about 30% to 100% between 4 week and 24 weeks of implantation, from about 40% to 100% between 4 week and 24 weeks of implantation, or from about 50% to 100% between 4 week and 24 weeks of implantation.

In some embodiments, the biologically functional scaffold and/or implant may comprise fibers or fiber bundles having an average diameter of about 0.1, 0.5, 1, 3, 5, 10, 20, 30, 40, 50, 60, 70, 80, 90, 100, 110, 120, 130, 140, 150, 200, 250, 300, 350, 400, 450, 500 µm or more. In additional embodiments, the biologically functional scaffold and/or implant may comprise fibers or fiber bundles having an average diameter of about 0.1, 0.5, 1, 3, 5, 10, 20, 30, 40, 50, 60, 70, 80, 90, 100, 110, 120, 130, 140, 150, 200, 250, 300, 350, 400, 450, 500 µm or less. In further embodiments, the biologically functional scaffold and/or implant may comprise fibers or fiber bundles having an average diameter from about 0.1 µm to about 500 µm, from about 0.1 µm to about 200 µm, from about 1 µm to about 500 µm, from about 10 µm to about 500 µm, from about 100 µm to about 1000 µm, or from about 100 µm to about 500 µm.

In some embodiments, the biologically functional scaffold and/or implant may comprise sheets having an average diameter of about 5, 10, 20, 30, 40, 50, 60, 70, 80, 90, 100, 110, 120, 130, 140, 150, 200, 250, 300, 350, 400, 450, 500, 1000, 3000, 5000 µm or more. In additional embodiments, the biologically functional scaffold and/or implant may comprise sheets having an average diameter of about 50, 60, 70, 80, 90, 100, 110, 120, 130, 140, 150, 200, 250, 300, 350, 400, 450, 500 μm or less. In further embodiments, the biologically functional scaffold and/or implant may comprise fibers and/or sheets having an average diameter from about 51 μm to about 500 μm, from about 51 μm to about 1000 μm, from about 100 μm to about 800 μm, from about 60 μm to about 500 μm, from about 100 μm to about 1000 μm, or from about 100 μm to about 500 μm.

In some embodiments, the biologically functional scaffold and/or implant comprises fibers, fiber bundles and/or sheets having an average length of 5 μm, 10 μm, 50 μm, 100 μm, 1000 μm, 5000 μm, 1 cm, 2 cm, 5 cm, 10 cm, 12 cm, 15 cm, 20 cm, 25 cm, or 50 cm or more. In some embodiments, the biologically functional scaffold and/or implant comprises fibers, fiber bundles and/or sheets having an average length of 5 μm, 10 μm, 50 μm, 100 μm, 1000 μm, 5000 μm, 1 cm, 2 cm, 5 cm, 10 cm, 12 cm, 15 cm, 20 cm, 25 cm, or 50 cm or less. In additional embodiments, the biologically functional scaffold and/or implant comprises fibers, fiber bundles and/or sheets having an average length from about 5 μm to about 50 cm, from about 100 μm to about 50 cm, from about 1000 μm to about 50 cm, from about 1 cm to about 50 cm, from about 1 cm to about 30 cm, from about 1 cm to about 20 cm, or from about 1 cm to about 15 cm. In preferred embodiments, the biologically functional scaffold and/or implant comprises dispersed soft tissue sheets with randomly interwoven or intertwined collagen fiber and collagen fiber bundle.

In some embodiments, the biologically functional scaffold and/or implant is in a form of a pocket, comb, hollow cylinder, triangular pyramid, rod, sheet, cube, tube, cup, concave, crescent, particle, sphere, ellipsoid, wedge, or ribbon. In additional embodiments, the biologically functional scaffold and/or implant may have an average length of 5 μm, 10 μm, 50 μm, 100 μm, 1000 μm, 5000 μm, 1 cm, 2 cm, 5 cm, 10 cm, 12 cm, 15 cm, 20 cm, 25 cm, or 50 cm or more. In some embodiments, the biologically functional scaffold and/or implant may have an average length of 5 μm, 10 μm, 50 μm, 100 μm, 1000 μm, 5000 μm, 1 cm, 2 cm, 5 cm, 10 cm, 12 cm, 15 cm, 20 cm, 25 cm, or 50 cm or less. In additional embodiments, the biologically functional scaffold and/or implant may have an average length from about 5 μm to about 50 cm, from about 100 μm to about 50 cm, from about 1000 μm to about 50 cm, from about 1 cm to about 50 cm, from about 3 cm to about 40 cm, from about 3 cm to about 30 cm, from about 3 cm to about 20 cm, or from about 3 cm to about 10 cm.

In another aspect, the method of the present invention described herein may comprise sieving the dispersed soft tissue, for example, on a sieve, mesh, or grid having pore size of about 0.5, 1, 2, 3, 4, 5, 6, 7, 8, 9, 10, 13, 16, 17, or 20 mm or less. In another aspect, the method described herein may comprise sieving the dispersed soft tissue, on a sieve, mesh, or grid having pore size of about 0.5, 1, 2, 3, 4, 5, 6, 7, 8, 9, 10, 13, 16, 17, or 20 mm or more. In another aspect, the method described herein may comprise sieving the dispersed soft tissue, on a sieve, mesh, or grid having pore size diameter from about 0.5 to 20 mm, from about 1 to 10 mm, from about 2 to 10 mm, from about 2 to 8 mm, or from about 2 to 6 mm. In another aspect, the method described herein may further comprise placing the dispersed soft tissue in a mold having a predetermined shape, wherein the dispersed soft tissue is frozen, dried, or freeze-dried in the mold. In another aspect, the method described herein may further comprise storing the biologically functional scaffold and/or implant prior to implanting. In some embodiments, the biologically functional scaffold and/or implant is stored in a dry state, in cryopreservation, or in a wet state. In additional embodiments, the method describe herein may further comprise treating the biologically functional scaffold and/or implant with a water replacing agent. In further embodiments, the biologically functional scaffold and/or implant may be stored in a wet state. In yet further embodiments, the water replacing agent comprises one or more selected from the group consisting of glycerol (glycerin USP), adonitol, sorbitol, ribitol, galactitol, D-galactose, 1,3-dihydroxypropanol, ethylene glycol, triethylene glycol, propylene glycol, glucose, sucrose, mannitol, xylitol, meso-erythritol, adipic acid, proline, hydroxyproline, polyethylene glycol, alcohol, and lipids. In another aspect, the method described herein may further comprise plasticizing the biologically functional scaffold and/or implant as described in U.S. Pat. Nos. 6,293,970, 6,569,200, 6,544,289, 7,063,726, or U.S. Patent Application Publication No. 2010/0030340, 2014/0180437, 2011/0015757, and 2013/0218294, each of which is incorporated by reference herein by its entirety.

In another aspect, the methods described herein may also comprise treating said biologically functional scaffold and/or implant with one or more treatment solutions before or after freezing drying, and/or freeze drying (or before or after other methods for drying the scaffold, besides freeze drying, such as air dry or drying in a drying oven at a pre-set temperature). In some embodiments, the method described herein may also comprise treating said biologically functional scaffold and/or implant with one or more treatment solutions after freezing, drying, and/or freeze drying before implantation. In some embodiments, the treatment solution comprises an ionic, enzymatic, or chemical crosslinking agent, a photoactive agent, or a polymer. The ionic crosslinking agent may comprise one or more selected from the group consisting of calcium, barium, aluminum, strontium, copper, zinc, magnesium, manganese, cobalt, and iron. The enzymatic crosslinking agent may comprise one or more selected from the group consisting of transglutaminase, ethylenediamine, lysyl oxidase family, hexamethylene diisocyanate (HMDIC), dimethyl suberimidate (DMS), and dimethyl-3-3'-dithiobispropionimidate (DTBP). The chemical crosslinking agent comprises one or more selected from the group consisting of glutaraldehyde, glyceraldehyde, genipin, glucose or ribose, poly(ethylene glycol) diepoxide crosslinker, poly(ethylene glycol) diglycidyl ether, EDC and NHS, and acryl azide. The polymer may comprise one or more selected from the group consisting of native or modified collagen, gelatin, agarose, modified hyaluronic acid, fibrin, chitin, biotin, avidin, demineralized bone matrix, MATRIGEL®, HUMAN EXTRACELLULAR MATRIX®, proteoglycans, laminin, fibronectin, elastin, heparin, glycerol, sucrose octasulfate, polyethylene glycol, polymethylmethacrylate, polyurethane, acryloilmorpholine, N,N-dimethyl acrylamide, N-vinyl pyrrolidone and tetrahydrofurfuryl methacrylate, hydroxyapatite, polyurethane, and polylactic acid. Furthermore, it should be considered that besides freeze drying, other methods for drying the scaffold, such as air drying or drying in a drying oven at a pre-set temperature, can be used.

In another aspect, the method described herein may also comprise adding one or more bioactive supplement(s) to the one or more soft tissue(s), the dispersed soft tissue, or the biologically functional scaffold and/or implant. In some embodiments, the one or more bioactive supplement(s) is selected from a group consisting of a growth or differentiation factor of the FGF family, TGF-family, amelogenin family, IGF-1, PDGF, EGF, VEGF, HGF, PTHrP, Ihh, dexamethasone, insulin, transferrin, selenium, ITS, or ascorbate. The bioactive supplements may be growth factors, differentiation factors, cytokines, anti-microbial agents, enamel matrix derivative (EMD), or anti-inflammatory agents. The growth or differentiation factors may be for example, a growth factor of the FGF-family or TGF-family, IGF-1, PDGF, EGF, VEGF, HGF, PTHrP, Ihh (Indian Hedgehog Homolog), dexamethasone, insulin, transferrin, selenium, ITS supplement, ascorbate, or a combination thereof. The cytokines may include GM-CSF, G-CSF, TNF-α, IL-1β, IL-4, IL-6, IL-8, IL-10, SLP1, MCP1, MIP-1α, MIP-2, IL-18, angiopoietin, KGF, endothelin, IFN-α, or IFN-β. Examples of anti-inflammatory agents may include an IL-1βR antibody, TNF-α receptor antagonist, cyclooxygenase-2 specific inhibitors, MAP kinase inhibitors, NO synthase inhibitors, NF-κB inhibitors, or inhibitors of MMP. There are various fibroblast growth factors. As an example, the human FGF-family includes 22 members, FGF-1 through FGF-23. (There is no human FGF-15 because FGF-15 is the mouse ortholog of human FGF-19.) Examples of members of the TGF-family may include TGF-α and TGF-β superfamily. The TGF-β superfamily includes TGF-βs (such as TGF-β1, TGF-β2, TGF-β3), activins, inhibins, bone morphogenic factors (BMPs), modified BMPs, antimullerian hormone (AMH), myostatins, and others. There are 20 isotypes of BMPs. They may be separated into four subfamilies, for example, (1) BMP2 and BMP4; (2) BMP3 and BMP3B (also known as growth/differentiation factor 10 (GDF10)); (3) BMPs 5, 6, 7 and 8; and (4) GDFs 5, 6, and 7. In additional embodiments, the method described herein may also comprise adding one or more bioactive supplement(s) extracted from tissue comprising demineralized bone matrix, basement membrane, or submucosa matrix. In further embodiments, the method described herein may also comprise adding one or more antioxidants including, for instance, sodium nitroprusside, cartilage matrix glycoprotein (CMGP), vitamins C, vitamin E, selenium, N-Acetylcysteine (NAC) estradiol, glutathione, melatonin, resveratrol, flavonoid, carotene, aminoguanidine, or lycopene to protect bioactive components from oxygen-radical-induced damage antioxidants.

In another aspect, the method described herein may also comprise adding one or more agent(s) that have bioactive supplement binding site(s) to the one or more soft tissue(s), the dispersed soft tissue, or the biologically functional scaffold and/or implant. In some embodiments, the agents having bioactive supplement binding site(s) may comprise hyaluronan, heparin, heparin sulfate, keratin sulfate, dermatan sulfate, chondroitin sulfate, betaglycan, heparan sulfate proteoglycan, syndecan, biglycan, or decorin. In additional embodiments, the agent(s) that have bioactive supplement binding site(s) increases the affinity of growth factors, differentiation factors, cytokines, anti-microbial agents, or anti-inflammatory agents to said biologically functional scaffold and/or implant.

In another aspect, the method described herein may also comprise cutting the one or more soft tissue(s), prior to dispersing the soft tissue, to have a dimension of length and/or diameter of about 0.5, 1, 5, 10, 20, 50, 100, 200, 500 mm or more on average. In additional embodiments, the method described herein may also comprise cutting the one or more soft tissue(s) to have a dimension of about 1, 5, 10, 20, 50, 100, 200, 550 mm or less on average. In further embodiments, the method described herein may also comprise cutting the one or more soft tissue(s) to have a dimension from about 1 mm to about 60 cm, from about 1 mm to about 50 cm, from about 1 cm to about 30 cm, from about 1 cm to about 20 cm, or from about 1 cm to about 10 cm on average.

In another aspect, the method described herein may comprise cleaning and disinfecting the one or more soft tissue(s). In another aspect, the method described herein may also comprise cleaning and disinfecting the soft tissue, and removing extraneous tissues associated with the soft tissue. Soft tissues may be cut into small pieces to produce crudely fragmented soft tissue, and optionally triturated and washed with distilled/deionized endotoxin-free water and/or an aqueous solution, such as isotonic saline, among others. In processing, multiple "washes" or "cleaning" may be affected using volumes of aqueous solution that are 2, 5, 10, or 20 times the approximated volume of the tissue being processed, in some embodiments. The use of three such processing steps may affect an approximate 1:100, 1:500 or 1:1000 dilution of associated solubilizable elements rendering the tissue essentially free from such solubilizable elements. The dispersed soft tissue may include soft tissue that has been reduced to fibers, bundle, sheets, and other components that are uniformly small and evenly distributed. The dispersed soft tissue may optionally include at least one of water, aqueous solutions, for instance isotonic saline, and water miscible polar organic solvents. In some embodiments, the dispersed soft tissue and, optionally, at least one of a water miscible polar organic solvent, water and an aqueous solution, may be prepared by shear-induced shredding of soft tissue. A conventional blender may be used in preparing the dispersed soft tissue, in certain embodiments. In a preferred embodiment, the dispersion speed is set from low to medium speed for a conventional blender. In another aspect, the method described herein may also comprise devitalizing or decellularizing the one or more soft tissue(s) to remove cellular components in accordance with the methods described in U.S. Pat. Nos. 6,734,018, 7,338,757, 8,574,826, 6,743,574, and 8,563,232, and U.S. Patent Application Publication No. 2014/0065238A1 and 2014/0154663A1, each of which is incorporated by reference herein in its entirety. A devitalized process may be performed without damage to matrix and/or tissue structure of the soft tissue and may employ detergents, sarcosinates, endonuclease, and disinfecting agents. The matrix structure may include collagens, hyaluronins, elastins, fibronectins, laminins, mucopolysaccharides and proteoglycans, among other components. Soft tissue that is devitalized may have a thickness of about 30, 20, 15, 10, 8, 5, 3, 2, 1, 0.5, 0.1, 0.05 mm or less, in certain embodiments. Soft tissue that is devitalized may also have a thickness of about 30, 20, 10, 8, 5, 3, 2, 1, 0.5, 0.1, 0.05 mm or more. In another aspect, the method described herein may also comprise placing the biologically functional scaffold and/or implant in designed packages that will fit the shapes and dimensions of the scaffold and/or implant, and maintain the shapes and dimension until implantation (See, e.g., WO2014130953, incorporated herein by reference). In another aspect, the method described herein may also comprise sterilizing the one or more soft tissue(s), the dispersed soft tissue, or the biologically functional scaffold and/or implant. Sterilization may involve the use of ionizing radiation, in some embodiments. In other embodiments, the absorbed dose of ionizing radiation may be between about 8.0 KGy and about 50 KGy, between about 8.0 KGy and about 25 KGy, or between about 8.0 KGy and about 18 KGy. In some embodiments, the sterilizing step may include placing the packaged tissue repair implants having a porous sponge-like structure on dry ice and irradiating the packaged composition. In certain embodiments, sterilization may be performed at a temperature of between about −20° C. and −50° C. The implants of the present invention may be sterilized using gamma irradiation, disinfecting agents, supercritical carbon dioxide, ethylene oxide, or electronic-beam.

In another aspect, the method described herein may comprise adding one or more bone or cartilage fragment material(s) to the one or more soft tissue(s), the dispersed soft tissue, or the biologically functional scaffold and/or implant. In some embodiments, bone fragments material(s) comprise one or more selected from the group consisting of bone, cortical bone, cancellous bone, cortical cancellous bone, ceramics, hydroxyapatite, calcium phosphate, calcium sulfate, and calcium carbonate. The bone may be demineralized bone or non-demineralized bone. "Demineralized bone matrix (DBM)" as used herein refers to bone having less than about 8 wt % residual calcium. Demineralization involves treating a bone tissue to remove its inorganic mineral hydroxyapatite material. The level of demineralization of a bone tissue is defined by the amount (wt %) of residual calcium found in the demineralized bone. In some embodiments, the demineralized bone may still contain physiologically active levels of growth and differentiation factors (e.g., osteogenic/osteoinductive growth factors, such as bone morphogenetic proteins (BMPs) remaining from the initial bone even after the demineralization treatment. In further embodiments, the demineralized bone may contain collagen, glycosaminoglycans, osteocalcin, osteonectin, bone sialoprotein, osteopontin, and mixtures thereof. "Non-demineralized bone" as used in the present application refers to bone that has not been treated to remove minerals present such as, for example, hydroxyapatite. Certain biologically functional scaffold and/or implant of the present invention may include demineralized bone particles or fibers. Demineralized bone matrix may be prepared from cleaned and disinfected bone that have been freeze-dried or not freeze-dried and ground/fractured/milled into bone particles or fibers. Bone particles may be selected by, for example, using sieving devices (i.e., mesh sieves) commercially available for obtaining particles within a desired size range. Such demineralized bone particles may have an average diameter of between about 125 microns and about 4 mm; between about 710 microns and about 2 mm; between about 125 microns and about 500 microns; between about 125 microns and about 850 microns; between about 125 microns and about 710 microns; between about 250 and 1000 microns; or between about 250 microns and about 710 microns. Certain embodiments of the present invention may include demineralized bone particle that is commercially available. For example, a suitable demineralized bone particle that is widely and reliably available is produced by LifeNet Health, Virginia Beach, Virginia Some biologically functional scaffold and/or implant of the present invention may include demineralized bone fibers. In certain embodiments, the demineralized bone fibers may have an average thickness of between about 0.1 mm and about 0.3 mm and an average width of between about 0.3 mm and about 1.0 mm. The length of the fibers may vary. In some embodiments, the demineralization process begins by producing bone particles having an average diameter size range of between about 1 mm and about 2 mm or bone fibers having an average dimension of 0.1 mm to 0.5 mm thickness and an average width of about 0.3 mm to about 1 mm. The fragments may be treated with cleaning solutions. If the bone to be processed into fragments has not been previously cleaned and/or disinfected, they may be cleaned and/or disinfected by the use of detergents, hydrogen peroxides, antibiotics, acids, and/or alcohols to affect a removal of associated tissues such as bone marrow and cellular elements. Following cleaning and disinfection, these fragments (i.e., particles and fibers) may be demineralized by exposure to dilute hydrochloric acid to affect a removal/reduction of the mineral component of the bone fragments (i.e., particles and fibers). Such additional processing may, in some instances, inactivate potential viral contamination (i.e., HIV and hepatitis viruses, among others).

In another aspect, the method described herein may or may not comprise processing the dispersed soft tissue under negative hydrostatic pressure before being frozen, dried, or freeze-dried to increase porosity. Three-dimensional (3-D) macro-porous structure in the present invention is designed to provide support for the cells until they are organized into a functioning tissue. After implantation, the architecture of the macro-porous structure can control the extent of vascularization and tissue ingrowth. The pore size and volume can be adjusted by adding porogens, application of inert gas, or application of a negative hydrostatic pressure before or after freeze-drying the biologically functional scaffold and/or implant.

In one aspect, the invention relates to a biologically functional scaffold and/or implant prepared by methods described herein. For example, the biologically functional scaffold and/or implant may comprise one or more soft tissue(s) dispersed at a temperature between about 0-50° C.

In one aspect, the invention also relates to methods of repairing a defect(s) in a tissue comprising implanting the biologically functional scaffold and/or implant described herein at the site of defect. The tissues with the defect may be bone tissues, cartilage, or soft tissues. Examples of soft tissues with the defect may include tendon, ligament, dermis, skin, vocal cord, nerve, bladder, vagina, urethral, heart, subcutaneous tissue, fascia, breast, muscle, placental membrane, placenta, and rotator cuff. In another aspect, the tissues with the defect may be in the musculoskeletal system, digestion system, cardiovascular system, respiratory system, urinary system, reproductive system, nervous system, and/or immune system. In some embodiments, the method excludes rehydration of the biologically functional scaffold and/or implant prior to implanting to allow said biologically functional scaffold and/or implant to absorb blood, fluid, and/or autologous cells in situ. Alternatively, implantation of a tissue repair implant into a human or animal can be conducted by rehydrating the tissue repair implant with a rehydrating solution; optionally seeding vital cells on the tissue repair implant to render the tissue repair implant vital; optionally culture the cell-seeded tissue repair implant before implantation; and implanting the tissue repair implant into the defect. In another aspect, the method may further comprise rehydrating the biologically functional scaffold and/or implant with a rehydrating solution; optionally seeding vital cells on said biologically functional scaffold and/or implant to render said biologically functional scaffold and/or implant vital; and optionally culture said cell-seeded biologically functional scaffold and/or implant before implantation. In some embodiments, the rehydrating solution comprises one or more selected from the group consisting of blood or bone marrow aspirate, platelet rich plasma, cerebrospinal fluid, synovial fluid, enzymes, bioactive supplements, natural polymers, synthetic polymers, photoactive agents, antioxidants, crosslinking agents, antimicrobial agents, vital cells, and one or more agents that have bioactive supplement binding site(s). In additional embodiments, the vital cells comprise one or more selected from the group consisting of cells from autologous or allograft bone marrow aspirate; stromal cells and/or stem cells from bone marrow; stromal cells and/or stem cells from fat, liposuction, synovium, periosteum, perichondrium, muscle, dermis, umbilical cord blood, placenta, placental membrane, and Wharton's jelly; and pericytes.

In one aspect, the invention also relates to methods of cell culture comprising culturing cells on the biologically functional scaffold and/or implant described herein. As used herein, cell culture refers to the maintenance of cells in an artificial environment, commonly referred to as an in vitro environment. The term cell culture is a generic term and may be used to encompass the cultivation not only of individual cells, but also of tissues, organs, organ systems or whole organisms. The cells used in the culture methods disclosed herein can be any prokaryotic or eukaryotic cell. The cell type used in the culture methods disclosed herein need not be from the same species from which the cell support compositions derive. In addition, the cells may be from an established cell line, or they may be primary cells or genetically engineered cells.

For example, the invention provides for growing and/or culturing cells on the biologically functional scaffold and/or implant described herein. "Growing and/or culturing cells on the biologically functional scaffold and/or implant" includes traditional cell culture methods as well as placing on a surface of the biologically functional scaffold and/or implant in any setting, such as in natural or synthetic biocompatible matrices or tissues. The cells may be mammalian, such as but not limited to human, bovine, porcine, murine, ovine, equine, canine, feline and others. In some embodiments, the cells that are cultured on the biologically functional scaffold and/or implant are stem cells. As used herein, the term "stem cell" is used as it is in the art and refers to cells that have the capacity for self-renewal and are capable of forming a least one specialized cell type. See, e.g., Donovan, P. J., Gearhart, J., Nature 414: 92-97 (2001). For instance, a stem cell can divide and give rise to one daughter cell that may be at least partially differentiated and to another daughter cell that retains the developmental potential of the mother cell. As used herein, stem cells can be adipose derived stem cells, dental pulp stem cells, adult stem cells (ASCs), embryonic stem cells (ESCs), committed progenitor cells, and/or induced pluripotent stem cells (iPSCs). In further embodiments, the biologically functional scaffold and/or implant can be used in in vitro methods for supporting cell growth and proliferation as well as for increasing osteogenesis, chondrogenesis, or ligament/tendon genesis in the stem cells cultured on the biologically functional scaffold and/or implant.

In some embodiments, the cells may be mesenchymal stem cells, such as adipose-derived stem cells, embryonic stem cells, progenitor cells, differentiated cells, undifferentiated cells, and/or induced-pluripotent stem cells. Appropriate cells may also include, but are not limited to cells of the ectodermal lineage, cells of the mesodermal lineage, and cells of the endodermal lineage. Examples of cells of the ectodermal lineage include but are not limited to keratinocytes, neurons. Examples of cells of the mesodermal lineage include but are not limited to myoblasts, adipocytes, preadipocytes, fibroblasts, endothelial cells, osteoblasts, chondrocytes, or stromal cells. Examples of cells of the endodermal lineage include but not limited to epithelial cells of the auditory tube, the respiratory tract, such as trachea, bronchi, and alveoli of the lungs, the gastrointestinal tract, the urinary bladder and epithelial cells lining all glands. The cells may also be primary cells derived from tissues or organs. Appropriate cell lines used in the present invention may include but are not limited to mesenchymal cell lines, preosteoblastic cell lines, osteoblastic cell lines, and chondroblastic cell lines.

In some embodiments, the cells may be derived from autologous or allogeneic sources. The cells may be differentiated cells including chondrocytes, adipocytes, osteoblasts, osteoclasts, endothelial cells, epithelial cells, fibroblasts, and periosteal cells. Additionally, the cells may be totipotent, pluripotent, multipotent, progenitor, or adult somatic stem cells. The stem cells may be derived from embryos, placenta, bone marrow, adipose tissue, blood vessel, amniotic fluid, synovial fluid, synovial membrane, pericardium, periosteum, dura, peripheral blood, umbilical blood, placental membrane, menstrual blood, baby teeth, nucleus pulposus, brain, neonatal foreskin, skin, hair follicle, intestinal crypt, neural tissue, muscle. The cells may be derived from skeletal muscle, smooth muscle, and cardiac muscle. The stem cells may be derived from genetic reprogramming of mature cells, such as induced pluripotent stem cells (iPSCs). All cells may further be derived from living or recently deceased donors.

Any cell described herewith may be cultured on the biologically functional scaffold and/or implant described herein for between about 15 minutes and about 4 weeks, about 2 hours and about 2 weeks, about 2 hours and about 1 week, about 2 hours and about 72 hours, about 24 hours and about 72 hours, or about 24 hours and about 96 hours, at between about 20° C. and about 40° C. or about 30° C. and about 37° C., in an atmosphere containing between about 1% $CO_2$ and about 10% $CO_2$ or about 4% $CO_2$ and about 6% $CO_2$, in certain embodiments. In some embodiments of the present invention, cells may be cultured in the presence of one or more growth factors described herein and (1) a tissue or an organ, (2) a matrix, or (3) a combination thereof. Cells that have been cultured in the presence of one or more growth factors described herein in a cell culture medium may subsequently be applied to a matrix, a tissue, an organ or a combination thereof, in certain embodiments.

The invention also relates to methods of promoting osteoinductivity, with the methods comprising culturing cells on the biologically functional scaffold and/or implant described herein. As used herein, "osteoinductivity" can refer to causing cells to differentiate into cells that are more osteoblast-like in phenotype, or the term can refer to increasing the proliferation of osteoblasts, or both. The cells, prior to culture on the biologically functional scaffold and/or implant, may be undifferentiated or partially differentiated cells. The cells may be present in culture or in a tissue, organ or portion thereof or in an organism. The osteoinductive activity of the biologically functional scaffold and/or implant may or may not be altered, including but not limited to, enhanced activity, relative to a control.

The invention also relates to methods of promoting chondroinductivity, with the methods comprising culturing cells on the biologically functional scaffold and/or implant described herein. As used herein, "chondroinductivity" can refer to causing cells to differentiate into cells that are more chondrocyte-like in phenotype, or the term can refer to increasing the proliferation of chondrocytes, or both. The cells, prior to culture on the biologically functional scaffold and/or implant, may be undifferentiated or partially differentiated cells. The cells may be present in culture or in a tissue, organ or portion thereof or in an organism. The chondroinductive activity of the biologically functional scaffold and/or implant may or may not be altered, including but not limited to, enhanced activity, relative to a control.

The invention also relates to methods of promoting adipogenesis/adipoinductivity, with the methods comprising culturing cells on the biologically functional scaffold and/or implant described herein. As used herein, "adipoinductivity" can refer to causing cells to differentiate into cells that are more adipocyte-like in phenotype, or the term can refer to increasing the proliferation of adipocytes, or both. The cells, prior to culture on the biologically functional scaffold and/or implant, may be undifferentiated or partially differentiated cells. The cells may be present in culture or in a tissue, organ or portion thereof or in an organism. The adipoinductive and adipoconductive activity of the biologically functional scaffold and/or implant may or may not be altered, including but not limited to, enhanced activity, relative to a control.

The invention also relates to methods of promoting ligament/tendon differentiation, with the methods comprising culturing cells on the biologically functional scaffold and/or implant described herein. As used herein, "ligament/tendon differentiation" can refer to causing cells to differentiate into cells that are more ligament and/or tendon-like in phenotype, or the term can refer to increasing the proliferation of ligament and/or tendon, or both. The cells, prior to culture on the biologically functional scaffold and/or implant, may be undifferentiated or partially differentiated cells. The cells may be present in culture or in a tissue, organ or portion thereof or in an organism. The ligament/tendon differentiation activity of the biologically functional scaffold and/or implant may or may not be altered, including but not limited to, enhanced activity, relative to a control surface.

There are variety of osteoblast, chondrocyte, adipocyte, ligament/tendon differentiation markers that can be measured to assess osteoinductivity, chondroinductivity, adipoinductivity, or ligament/tendon differentiation, respectively. For example, cells express alkaline phosphatases during the early stages of differentiation toward osteoblast lineages. Therefore, in vitro alkaline phosphatase assays may be used to evaluate osteoinductivity in cells cultured on the biologically functional scaffold and/or implant described herein. The ability of the biologically functional scaffold and/or implant to stimulate or induce the alkaline phosphatase expression in an otherwise non-bone forming cells, such as myoblast (C2C12 cells), would indicate that the biologically functional scaffold and/or implant has osteoinductive activity. In these assays, cells cultured on the biologically functional scaffold and/or implant and on a control surface are used as negative controls to show that the baseline alkaline phosphatase expression on non-bone forming cells. The baseline of the osteoblastic markers in the negative control need not be zero, meaning that the cells in the negative control group may have at least some level of phenotypic marker(s). Accordingly, an "osteoinductive" surface of the biologically functional scaffold and/or implant would simply cause an increase in the osteoblastic markers in experimental cells. Similarly, chondrocyte markers, including but not limited to type X collagen, type II collagen, Sox 9, Aggrecan. Matrilin-1 and CEP-68, to name a few, can be used to assess chondroinductive potential. Adipogenesis markers include but not limited to adiponectin, perilipin, leptin, FATP (1, 2, 4, 5, 6), and peroxisome proliferator-activated receptor gamma (PPAR gamma). Moreover, ligament/tendon markers, including but not limited to scleraxis, can be used to assess ligament/tendon differentiation potential.

Moreover, osteoinductivity, chondroinductivity, adipoinductivity/adipoconductivity, and ligament/tendon differentiation may be determined in tissue culture by investigating the ability of the biologically functional scaffold and/or implant to differentiate or induce osteoblast phenotype, chondrocyte phenotype, adipocyte phenotype, ligament/tendon cell phenotype in cultured cells, such as primary cells, cell lines, or explants. For example, the cells may display increased production of a marker characteristic of osteoblasts, such as alkaline phosphatase, etc. For example, the osteoinductive, chondroinductive, adipoinductive, ligament/tendon differentiation potentials of the biologically functional scaffold and/or implant may be more than 0.2, 0.4, 0.6, 0.8, 1, 2, 3, 4, 5, 6, 7, 8, 9 or 10 times greater than a control. In another example, the osteoinductive, chondroinductive, adipoinductive/adipoconductive, ligament/tendon differentiation potentials of the biologically functional scaffold and/or implant described herein may be more than 10, 20, 30, 40, 50, 60, 70, 80, 90, 100, 500 or even 1000 times greater than those of a control scaffold.

Osteoinductivity, chondroinductivity, adipoinductivity/adipoconductivity, ligament/tendon differentiation, for assessing the bone, cartilage, adipose tissue, ligament or tendon forming potential induced by the biologically functional scaffold and/or implant in a location such as muscle, may also be evaluated using a suitable animal model. For example, intramuscular implantation into a rodent has been used as a model to assess osteoinductive activity of the biologically functional scaffold and/or implant.

The invention also relates to methods of promoting angiogenesis, hemostasis, biocompatability, infection resistance, cell attachment, proliferation or maintaining the differentiated state or preventing de-differentiation of osteoblasts, chondrocytes, ligament cells, tendon cells, fibroblasts, adipocytes, and/or any cell type disclosed herein with the methods comprising culturing the cells on the biologically functional scaffold and/or implant described herein. The proliferative activity of the biologically functional scaffold and/or implant may or may not be altered, including but not limited to, enhanced activity, relative to a control surface. The invention further relates to methods of promoting adipose tissue formation of adipocytes, fibroblasts, epithelial cells, and/or vascular endothelial cells. The invention also relates to methods of increasing or promoting angiogenesis, hemostatic function, biocompatibility, and/or infection resistance.

Mitogenicity may be assessed by investigating cell proliferation induced by the biologically functional scaffold and/or implant using various in vitro assays that measure metabolic activity, such as MTT [3-(4,5-dimethylthiazol-2-yl)-2,5-diphenyltetrazolium bromide] assay, alamarBlue® assay, and others. The alamarBlue® assay uses a non-cytotoxic reduction-oxidation indicator to measure cell metabolic activity, making it a nondestructive assay for assessing the mitogenic activity of the biologically functional scaffold and/or implant described herein. Proliferation can also be assessed by measuring DNA quantification, such as by using a PicoGreen™ DNA assay, radioactive labeling of DNA synthesis, such as [$^{3H}$]thymidine labeling or BrdU incorporation. Proliferation can also be assessed via manual cell counting, such as staining cells with trypan blue and counting with a hemacytometer.

The invention also relates to methods of increasing or promoting osteogenesis, chondrogenesis, ligament/tendon genesis, or adipogenesis of cells in the biologically functional scaffold and/or implant described herein. The methods may comprise culturing the cells on the biologically functional scaffold and/or implant described herein. As used herein, "osteogenesis" is the deposition of new bone material or formation of new bone, including, but not limited to, intramembranous osteogenesis and endochondral osteogenesis. As used herein, "chondrogenesis" is the deposition new cartilage material or formation of new cartilage. As used herein, "ligament/tendon genesis" is the deposition new ligament and/or tendon material or formation of new ligament and/or tendon. As used herein, "adipogenesis" is the deposition new adipose tissue or formation of new adipose tissue. The osteogenic, chondrogenic, adipogenic, ligament, or tendon inducing activity of the biologically functional scaffold and/or implant may or may not be altered, including but not limited to, enhanced activity, relative to a control surface. The cells may include cells in any tissue in which bone, cartilage, fat, ligament, or tendon formation is desired, such as, but not limited to, bone, cartilage, subcutaneous, breast, ligament, muscle, tendon, etc.

In certain embodiments, the biologically functional scaffolds and/or implant may be provided together with other scaffolds or devices, such as a surgical suture, a decellularized or non-decellularized tissue, a synthetic polymer or metallic cage, for treating or repairing soft tissues defects, osseus defects, or spinal injuries. Examples of soft tissue defects include breast tissue loss due to lumpectomy or mastectomy, rotator cuff tears and injuries, and ligament tears and injuries. As an example, the implants of the present invention may be combined with decellularized/devitalized dermis to repair, replace or treat breast tissue loss due to lumpectomy or mastectomy.

The invention also relates to methods of treating a tissue or organ defect or injury, for example, a musculoskeletal, dental or soft-tissue defect or injury, in an animal or human comprising administering cells seeded and/or cultured on the biologically functional scaffold and/or implant described herein to the tissue or organ defect (e.g. osseous defects, defects in cartilage, ligament, tendon, spinal disc, dental socket, breast, dermis, and tendon insertion site to bone).

The invention further relates to methods of treating a tissue or an organ defect or injury, for example a musculoskeletal, breast after lumpectomy or mastectomy, dental, lip, maxillofacial, or soft-tissue defect, in an animal by applying the biologically functional scaffold and/or implant described herein to the defect, and application to the defect may be accomplished by injecting the biologically functional scaffold into the defect, inserting the biologically functional scaffold between tissue or organ, wrapping the biologically functional scaffold around tissue or organ, or placing the biologically functional scaffold and/or implant on top of the defect.

In yet another embodiment, cells may be seeded onto the biologically functional scaffold and/or implant. The cells seeded on the biologically functional scaffold can be any cell, such as but not limited to, osteoblasts, chondrocytes, ligament cells, tendon cells, preadipocytes, progenitor cells, and stem cells disclosed herein or otherwise known in the art. The seeded cells may be allowed to proliferate and possibly attach to the biologically functional scaffold and/or implant.

In yet further embodiments, the present invention may also relate to drug delivery using the biologically functional scaffold and/or implant as a carrier. For example, the biologically functional scaffold and/or implant may encapsulate the bioactive supplements described herein and deliver such bioactive supplements to a site of interest.

Any of the methods of the present invention can be performed in virtually any setting, such as an in vivo, ex vivo, in situ or in vitro setting. For example, methods of promoting osteogenesis, chondrogenesis, or tendon/ligament inducing activities in cells may be performed in cell culture, may be performed in seeded cells on the biologically functional scaffold and/or implant, or may be performed in an intact organism. Moreover, any combination of any two or more of any of the embodiments described herein are contemplated.

While the invention has been described and illustrated herein by references to various specific materials, procedures and examples, it is understood that the invention is not restricted to the particular combinations of material and procedures selected for that purpose. Numerous variations of such details can be implied as will be appreciated by those skilled in the art. It is intended that the specification and examples be considered as exemplary, only, with the true scope and spirit of the invention being indicated by the following claims. All references, patents and patent applications referred to in this application are herein incorporated by reference in their entirety.

The following examples are illustrative and are not intended to limit the scope of the invention described herein.

EXAMPLES

Example 1: Preparation of Tissue Repair Implants

Skin from a human cadaver were procured and returned to the processing facility under sterile conditions. Donor histories, personal and medical, were obtained following accepted standards of the American Association of Tissue Banks. Microbiological tests were performed following FDA guidelines for testing sterility of products.

The skin pieces were cleaned of hair, unwanted adipose tissue and epithelial layer. The obtained dermis was treated with detergent containing N-lauryl sarcsinate and DNAase followed by saline rinse. The resulting cleaned and decellularized/devitalized dermis were used for the following experiments.

The dermis was cut into small (about 1.0 cm by 1.0 cm) pieces (e.g., crude fragments). About 24 grams of dermis and three ice cubes were mechanically dispersed (e.g., blended) together for 2 minutes using an Osterizer from Sunbeam-Oster, Inc., and three more pieces of ice cubes were added into the mixture and dispersed for another minute. (When reference is made to ice cubes (or ice pieces) in the Example section of the present application, it should be understood that each ice cube or ice piece is made with 10 mL of sterile ultraputure water, unless otherwise indicated). Then the processed soft tissue was transferred onto a sterile sieve. The undispersed tissue was picked out and mixed with two ice cubes and dispersed for another 2 minutes. Then the dispersed soft tissue was transferred back to the sterile sieve. The layer of dispersed soft tissue was transferred into molds (e.g. petri dishes or test tubes) and weighed. The molds containing dispersed soft tissue were stored at −20° C. or −80° C. freezer for a minimum of 4 hours, followed by freeze drying for 48-96 hours. The resultant porous soft tissue structure was then sent out for sterilization by gamma irradiation.

Example 2: Preparation of Tissue Repair Implants with Ice or Water

Method 1: Cleaned dermis was prepared as described in example 1 and cut into small (about 1.0 cm by 1.0 cm) pieces. About 12 grams of dermis and two ice cubes were mechanically dispersed (Osterizer from Sunbeam-Oster, Inc.) together for 2 minutes, and two more ice cubes were added into the mixture and dispersed for two minutes. Then the dispersed soft tissue was transferred onto a sterile sieve.

The undispersed tissue was picked out and mixed with two ice cubes and dispersed for another 2 minutes. Then the dispersed soft tissue was transferred onto the same sieve. The layer of dispersed soft tissue was transferred into molds and weighed.

Method 2: Another 12 grams of dermis (about 1.0 cm by 1.0 cm) pieces and 20 mL of ambient temperature sterile ultrapure water were mechanically dispersed (Osterizer from Sunbeam-Oster, Inc.) together for 2 minutes, and 20 mL of ambient temperature of sterile ultrapure water were added into the mixture and dispersed for two more minutes. Then the dispersed soft tissue was transferred onto a sterile sieve. The undispersed tissue was pick up and mixed with 20 mL of ambient temperature sterile ultrapure water and dispersed for another 2 minutes. Then the dispersed soft tissue was transferred onto the sterile sieve. The layer of dispersed soft tissue was transferred into molds and weighed.

The molds containing dispersed soft tissue (method 1 or method 2) were stored at −20° C. or −80° C. freezer for a minimum of 4 hours, followed by freeze drying for 48-96 hours.

Example 3: Characterization of Porous Soft Tissue Structure

Figure 1:
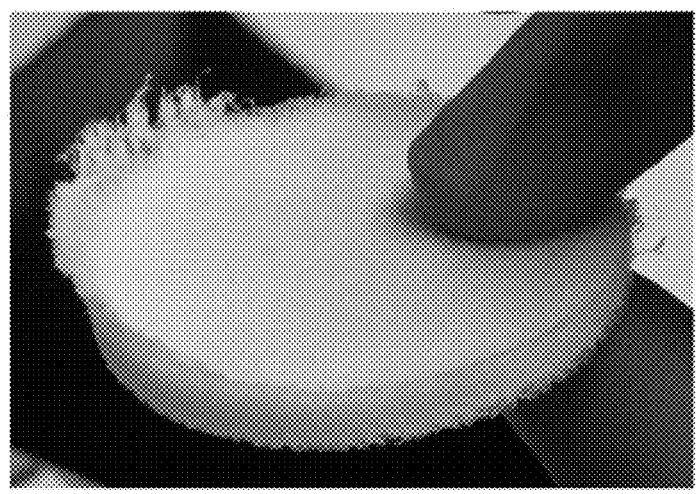
FIG. 1 depicts an exemplary porous soft tissue structure after freeze drying in disc shape.
Figure 2:
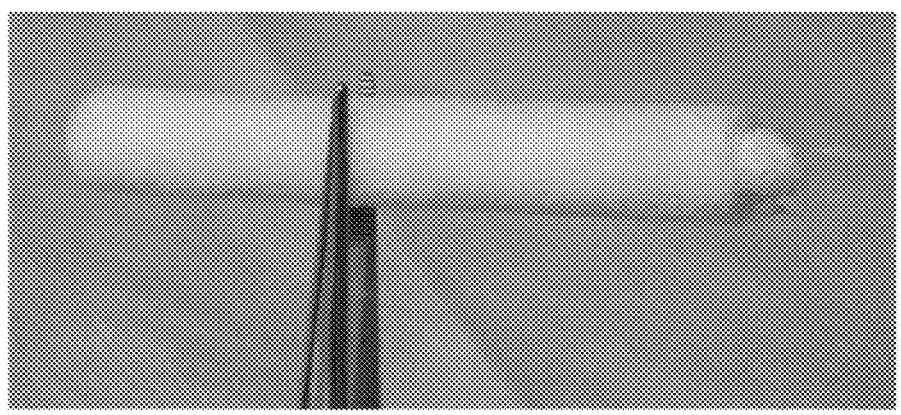
FIG. 2 depicts an exemplary porous soft tissue structure after freeze drying in cylinder shape.

Tissue repair implants having sponge-like structures were prepared according to the processing steps described in Example 1, and Example 2 and showed in FIGS. 1 and 2.

Figure 3:
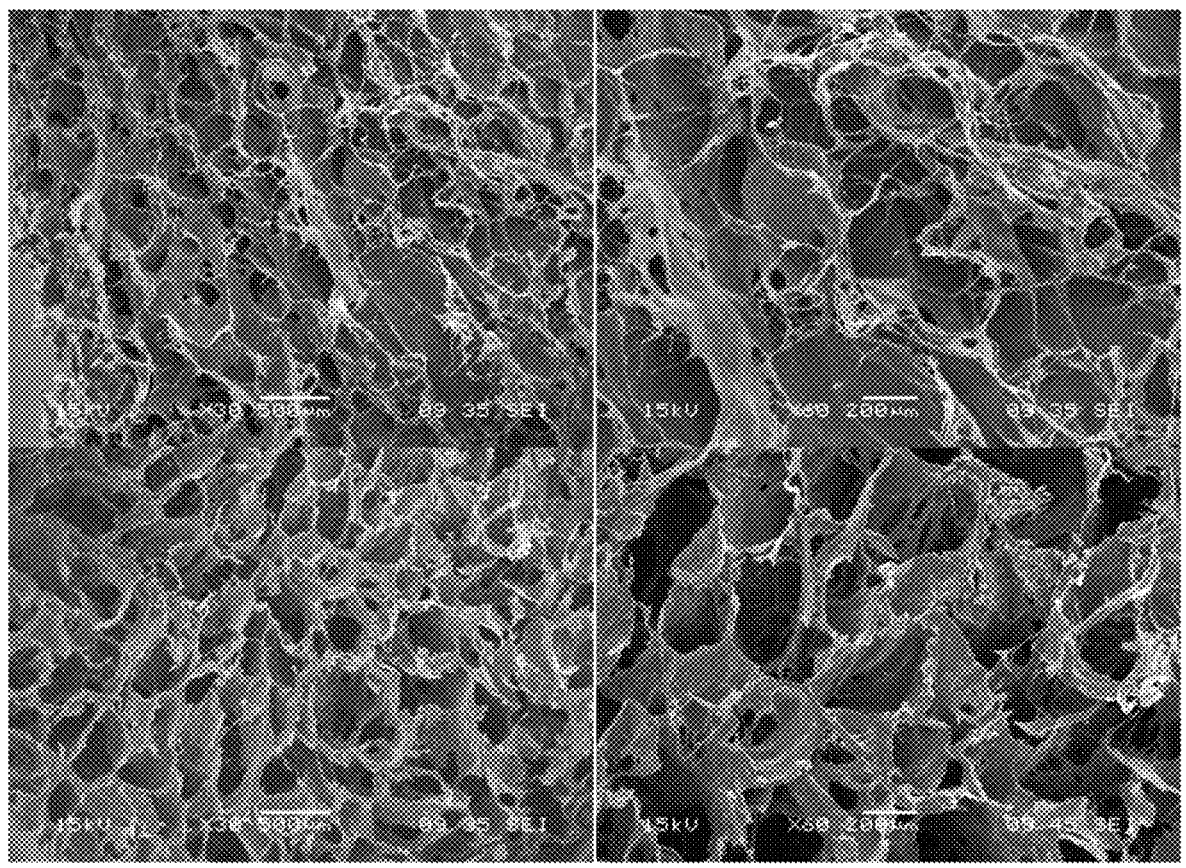
FIG. 3 depicts SEM photos of porous soft tissue structure made according to method 1 in Example 2 (30× and 60× magnification), showing web structure with pores and fibers.
Figure 4:
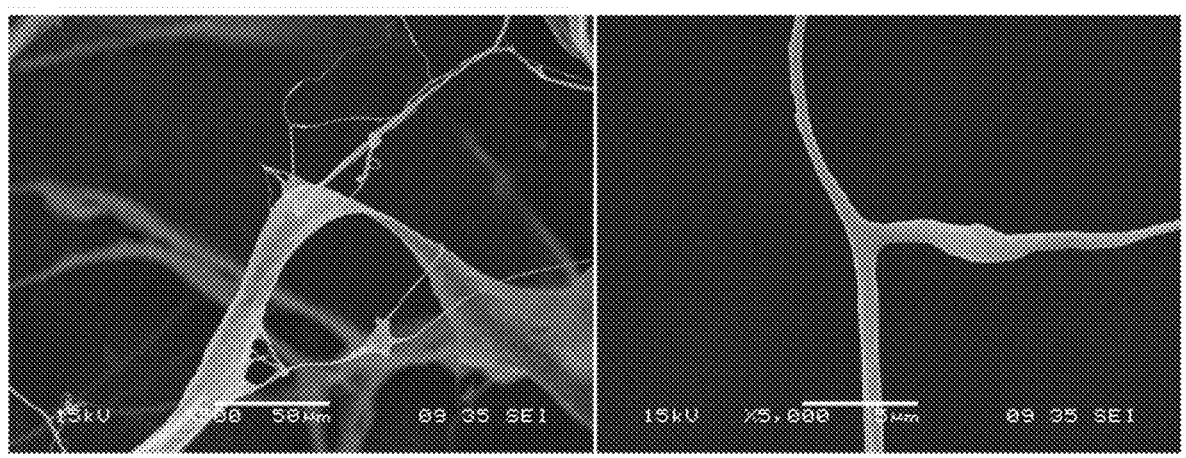
FIG. 4 depicts SEM photos of porous soft tissue structure made according to method 1 in Example 2 (500× and 5000× magnification), showing fibers.
Figure 5:
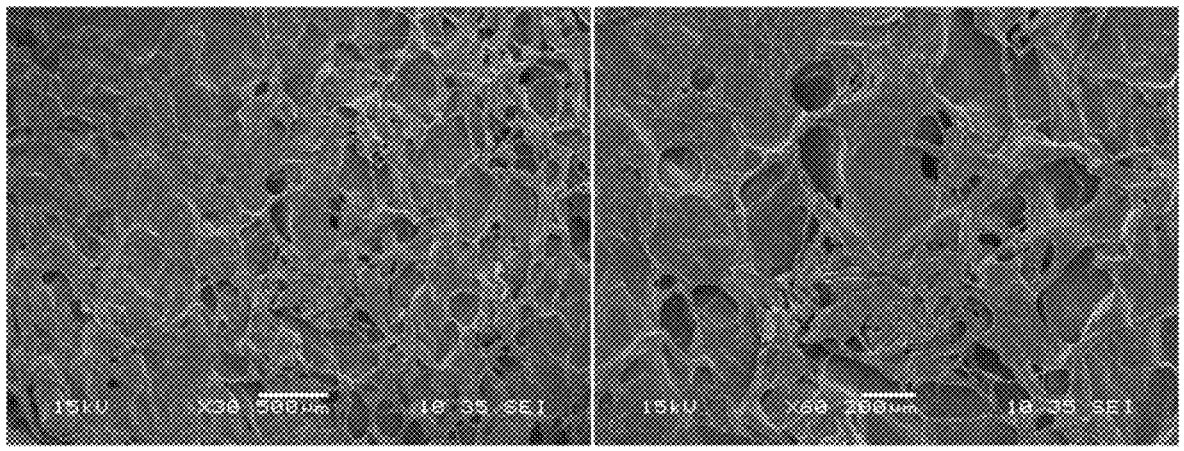
FIG. 5 depicts SEM photos of sponge-like soft tissue structure made according to method 2 in Example 2 (30× and 60× magnification), showing structure with pores and fibers.
Figure 6:
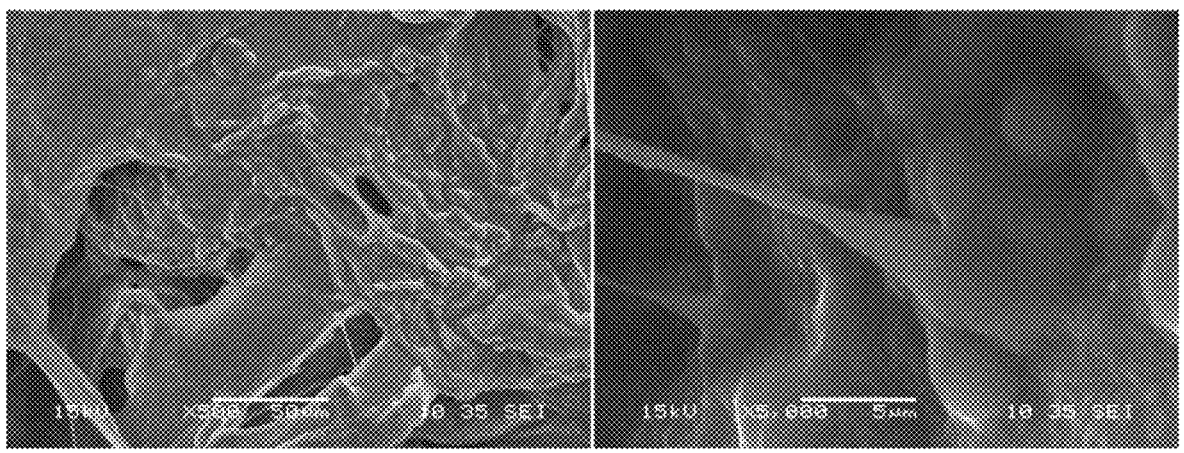
FIG. 6 depicts SEM photos of sponge-like soft tissue structure made according to method 2 in Example 2 (500× and 5000× magnification), showing fibers.

Porosity and fiber distribution in the porous sponge-like structure: Various prototypes of tissue repair implants having a sponge-like soft tissue structures were analyzed. Representative SEM pictures of porous sponge-like soft tissue structure were shown in FIGS. 3-6. FIGS. 3-4 showed the sponge like structure made using method 1 in example 2, FIGS. 5-6 showed the structure made using method 2 in example 2. It was found the framework of the porous sponge-like implant form web structures with pore sizes ranging from 10 µm to 500 µm in diameter. The fibers in the structure had the diameter ranging from 0.1 µm to 500 µm.

Figure 7:
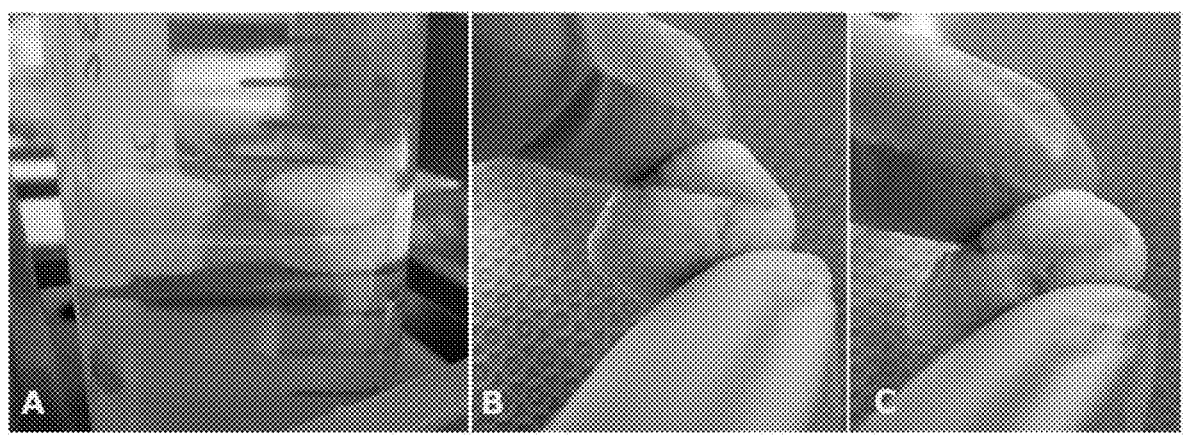
FIG. 7 depicts an exemplary porous soft tissue structure after immersed into sterile saline for one week, showing shape and size maintenance (A) and moldability (B and C).
Figure 8:
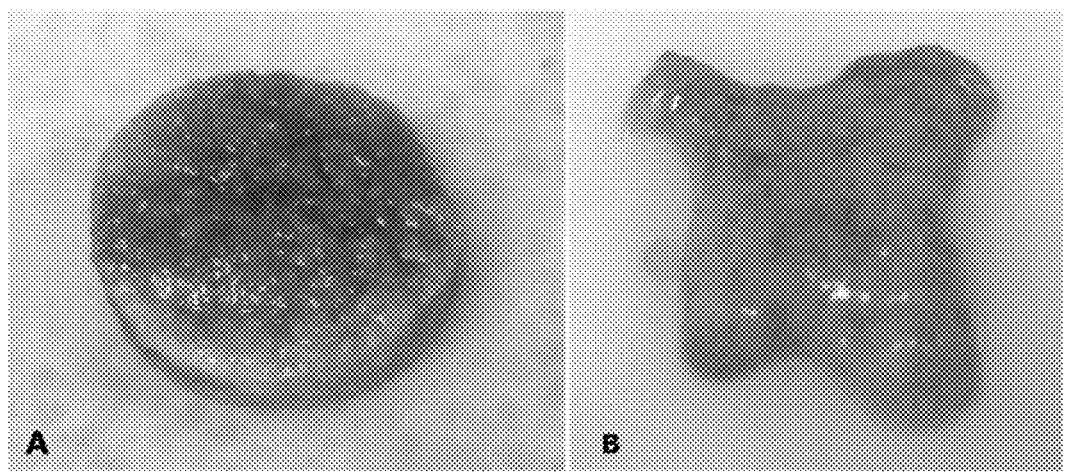
FIG. 8 depicts an exemplary porous soft tissue structure after hydration with sterile saline containing blue dye, showing the disc structure maintenance (A) and moldability (B).
Figure 21:
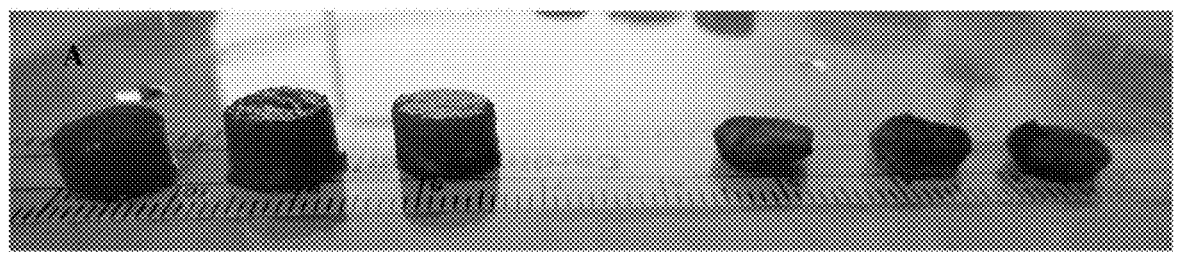
FIG. 21 depicts the exemplary porous soft tissue scaffolds made from dermis after hydration with sterile saline containing blue dye, showing the structure maintenance of the three discs at left side and the other three discs pressed to remove liquid at right side (A). The three disc structures that were pressed returned to their original shape after rehydration with saline (B).
Figure 21:
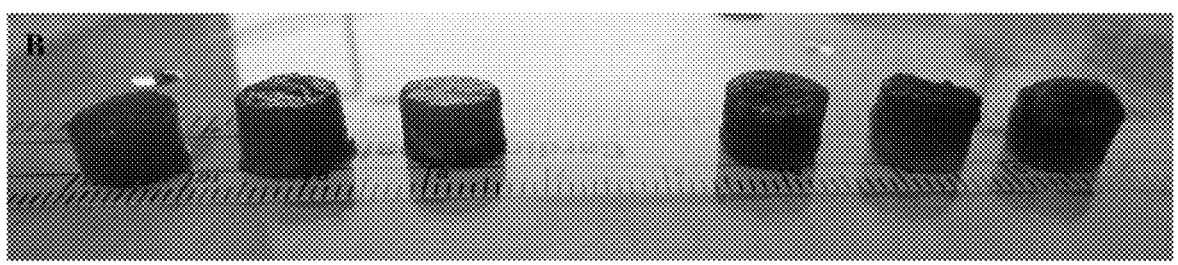

Hydration experiment: Representative samples were cut from the sponge-like soft tissue structure, some samples were immersed in sterile ultrapure water or saline for days to weeks to monitor the shape and size change, after 2 weeks of immersion, no shape change was found for these soft tissue structures (in FIG. 7, item A). Some samples were used for solution uptake assessment. The dry weight and size of each sample was determined. Then, the sample was placed on a weighing boat and added saline solution spiked with dye incrementally until visibly saturated in each sample (in FIG. 8, item A). The hydrated sample was transferred onto the weighing paper on analytical balance, and the wet weight was determined for each sample. The total weight of solution uptake was calculated by deduction of structure dry weight from the saturated wet weight. The solution uptake was about 3-10 times of the structure dry weight. Six samples were hydrated with saline solution spiked with dye, then three of the samples were compressed to remove liquid (FIG. 21A). New saline solution spiked with dye was injected back to compressed samples. The three sponge-like soft tissue structures were able to return to its original shape after rehydration (FIG. 21B).

Handling and shaping: The hydrated sponge-like soft tissue structures were molded with hands or pipet tips into various shapes (in FIG. 7, items B and C, and in FIG. 8, item B).

Example 4: In Vitro Biocompatibility

Figure 9:
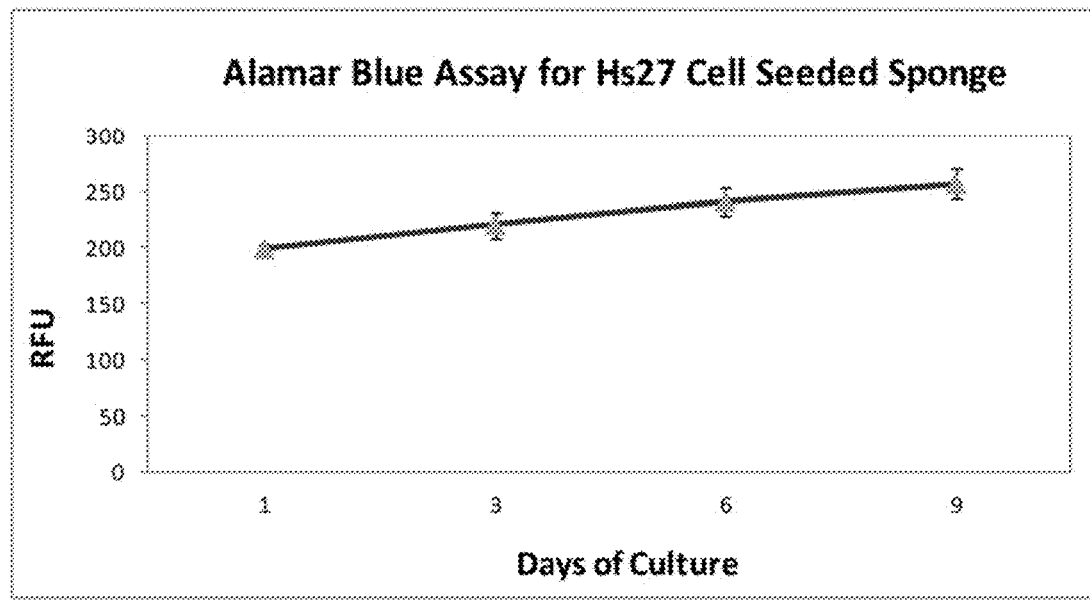
FIG. 9 depicts dermal fibroblasts growth in a porous soft tissue structure over 9 days of culture.
Figure 10:
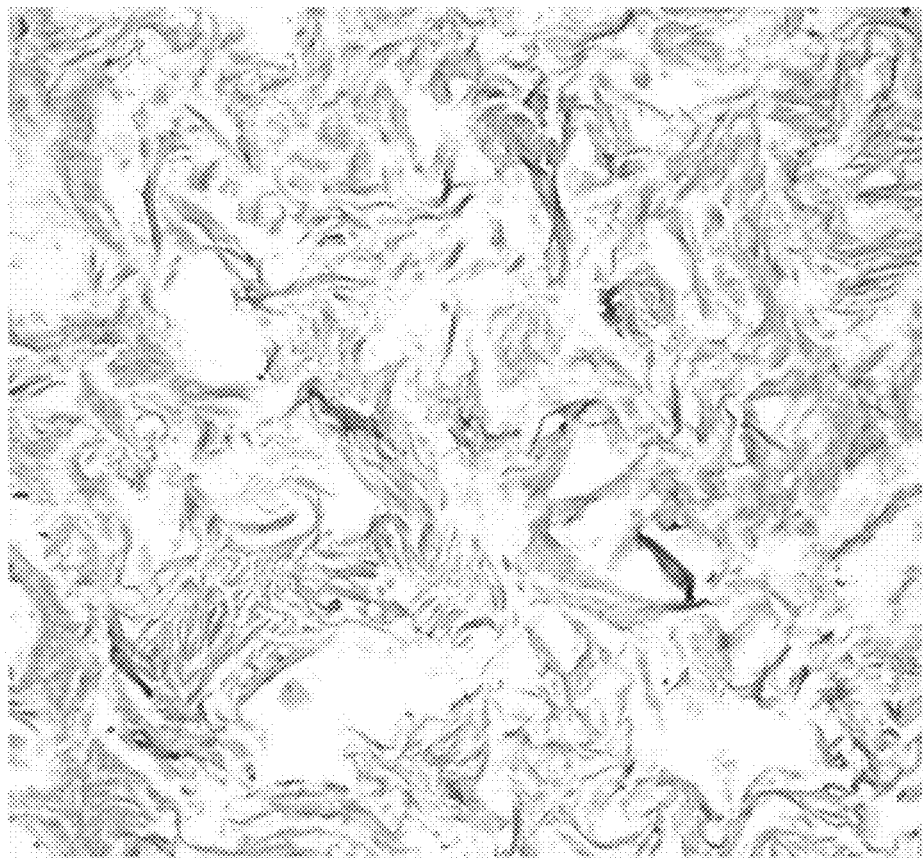
FIG. 10 depicts H&E staining of an exemplary porous soft tissue scaffold seeded with dermal fibroblasts (40×).

Human dermal fibroblast Hs27 cells (ATCC CRL-1634) were seeded directly on the surface of the sponge-like soft tissue structures at the density of $1\times10^6$ cells/cm$^2$ and cultured in 24-well plates pre-coated with 1.2% poly(2-hydroxyethyl methacrylate to prevent cell attachment to the culture plate. Cells seeded on the tissue culture plate pre-coated with 1.2% poly(2-hydroxyethyl methacrylate) were used as a control. Same seeding density was maintained for the sponge-like soft tissue structure group and the control group. AlamarBlue reagent (10%) was added into the culture media on day 1, day 3, day 6, and day 9 of the culture and incubated for 5 hours. The fluorescent intensity of the culture media with AlamarBlue reagent was measured. The intensity of the fluorescence is correspondent to the viability/metabolism of the cells, i.e., the higher the intensity the more viable/metabolic active cells. As shown in FIG. 9, the sponge-like soft tissue structure not only maintained the cell viability but also support cell growth as the cell number in the sponge-like soft tissue structure group increased steadily over nine days of culture. The control cells showed about 65% viability reduction on day 1 and 90% viability reduction on day 3, which suggests that this cell type is anchorage-dependent and have to be cultured on a suitable substrate that is specifically treated to allow cell adhesion and spreading. In addition, the sponge-like soft tissue structures maintained their integrity during the culture. H&E staining of one of the representative sponge-like soft tissue structure after 9 days of culture was shown in FIG. 10. The sponge-like soft tissue structure provided a suitable substrate for cell adhesion, spreading, and proliferation.

Example 5: Subcutaneous Implantation of Sponge-Like Soft Tissue Structure

The sponge-like soft tissue structures were prepared as described in Example 1. Two different thicknesses (2 mm and 4 mm) of soft tissue structure were made. Implant samples were generated by taking 8 mm biopsy punches from the freeze dried structures. Each punch was measured with calipers and weighed to confirm density and thickness. All soft tissue structure samples were terminally sterilized by gamma irradiation at 12.8-19.8 kGy absorbed dose on dry ice.

Male athymic mice (Nu/Nu Foxn1nu), about 6 weeks in age, were used for this study. The animals were weighed to the nearest 0.1 g and anesthesia was induced by isoflurane (1 to 5% in $O_2$ to effect) and maintained at 2 to 3% in $O_2$ for the surgery. Each animal received peri-operative analgesic Buprenorphine SR® at 0.5 to 1.0 mg/kg via subcutaneous injection and ophthalmic ointment was placed over the eyes. The dorsal region was swabbed twice with betadine and alcohol. An approximately 1 cm incision, one on each side of the dorsal midline was created. Two subcutaneous pockets approximately 0.15 cc were formed from these incisions using blunt dissection. The implant samples of the soft tissue structures were rehydrated with isotonic saline (50 µL) for a minimum of 5 minutes prior to implantation. The implants were inserted in the subcutaneous pocket. Each animal received a total of 2 implants. Incisions were closed with interrupted 4-0 prolene sutures and secured with a staple. Each animal was housed separately in a clean cage and monitored until the animal is alert and mobile.

After 4 weeks of implantation, animals were euthanized by $CO_2$ inhalation and their weights were recorded. The implant sites were carefully exposed by cutting the skin and subcutaneous tissues about 5 mm away from the implant. The implanted sample and the 3-5 mm of surrounding tissue were excised and fixed in 10% neutral buffered formalin (NBF) for a minimum of 4 days to achieve complete fixation.

Each explant sample was cut along its longest midline to create two halves. The resulting specimens were embedded together (cut face down) in the same paraffin block and histology sections were prepared. Two sections from each group were stained with hematoxylin and eosin (H&E). The section with the largest cross section of implant material was used for grading. Tissue sections were evaluated semi-quantitatively for fibroblast infiltration of the implant, degree of neovascularization, inflammatory cell response (macrophage/giant cells, neutrophils), and fibrous tissue/encapsulation.

Figure 11:
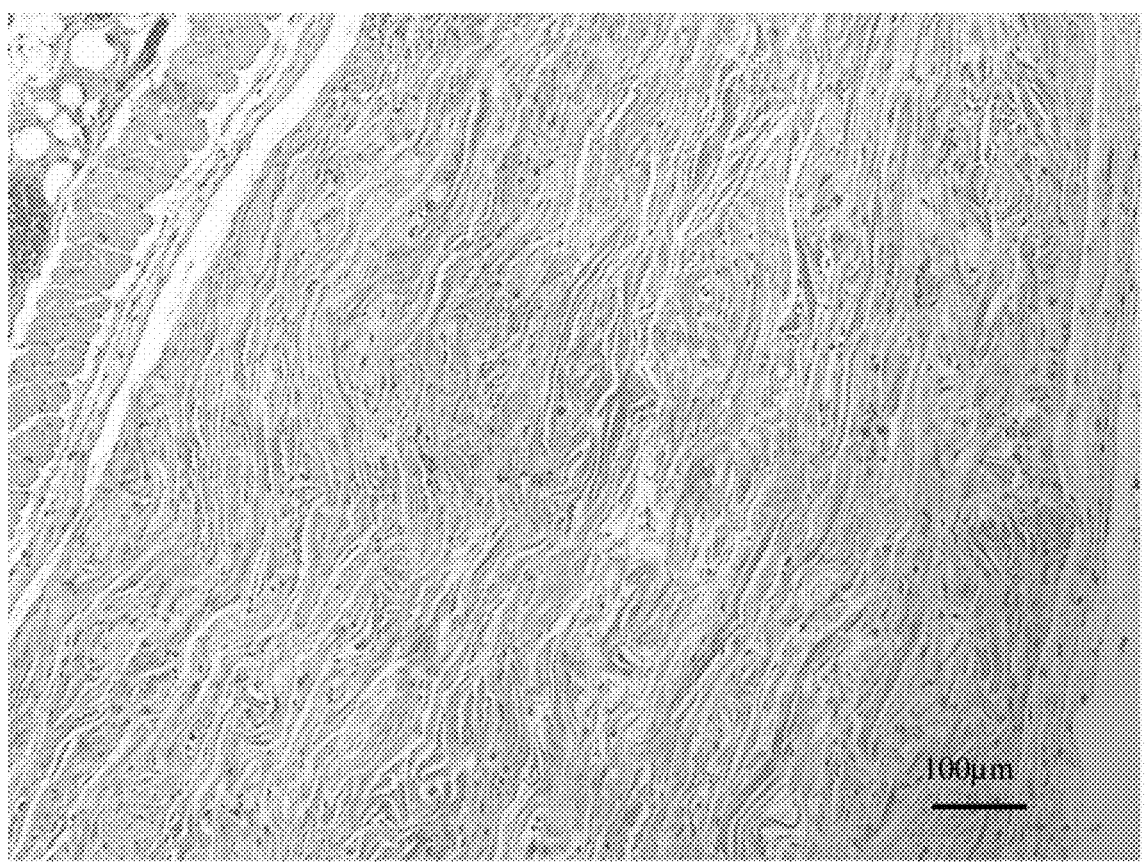
FIG. 11 depicts H&E staining of an exemplary thin porous soft tissue implant explantation after 4 weeks subcutaneous implant in an athymic mouse. Cell infiltration was found in full depth of the structure. No significant inflammation was found in the explants.
Figure 12:
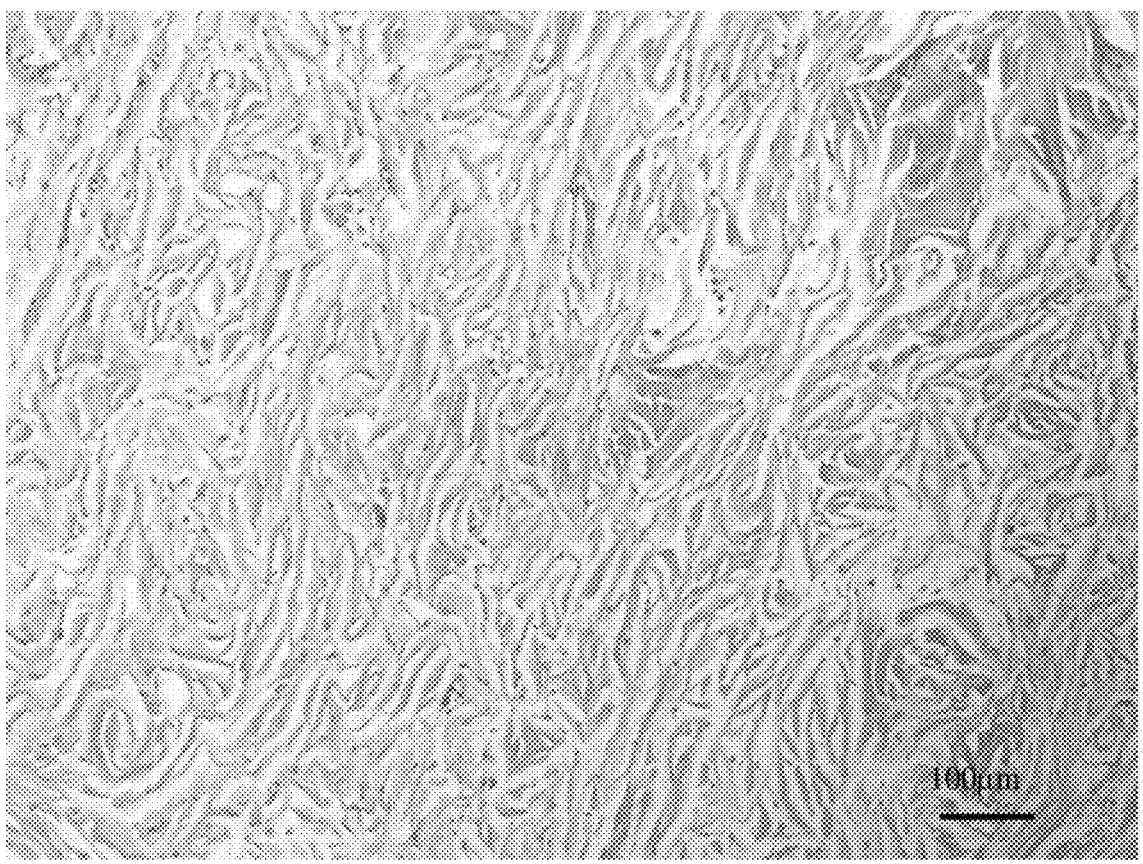
FIG. 12 depicts H&E staining of the thick porous soft tissue implant explantation after 4 weeks subcutaneous implantation in an athymic mouse. Cell infiltration was found in full depth of the structure. No significant inflammation was found in the explants.
Figure 13:
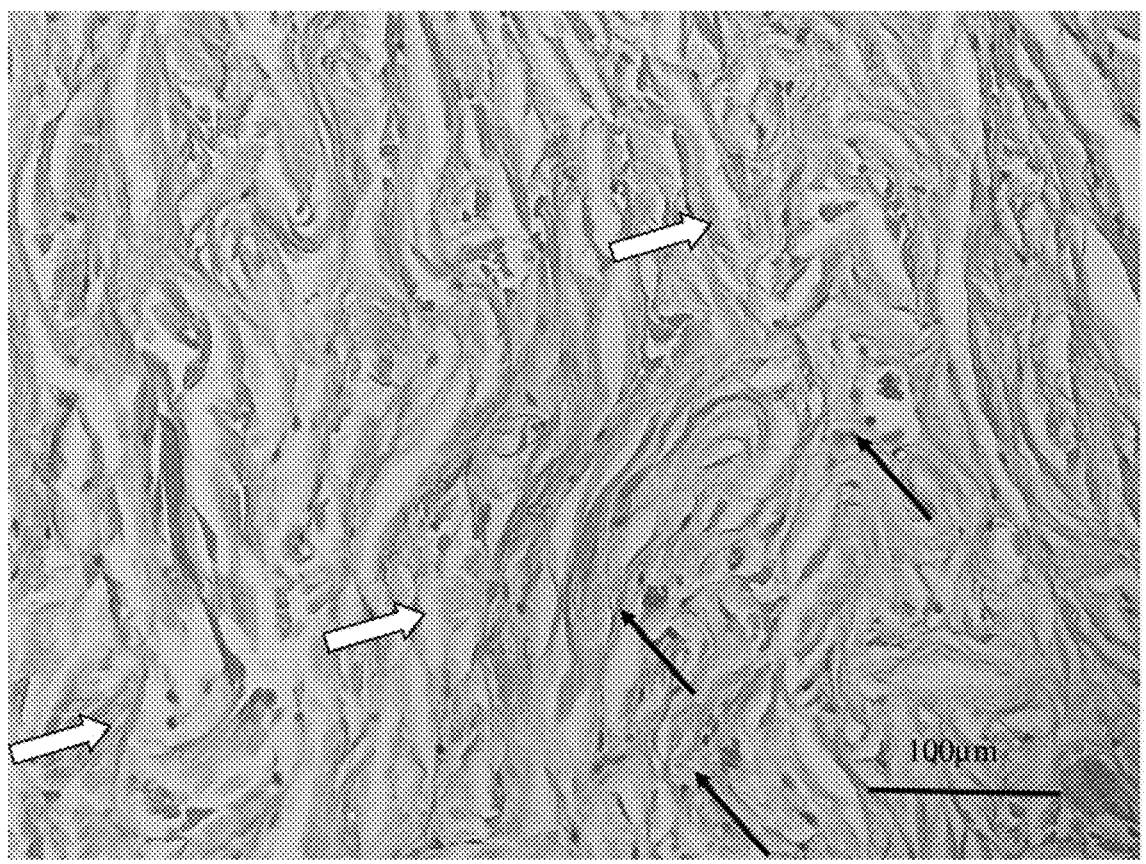
FIG. 13 depicts H&E staining of the porous soft tissue implant explanted after 4 weeks subcutaneous implantation in an athymic mouse. Arrows showed new blood vessels inside of the structure. Open arrows showed cells infiltrated into the structure. No significant inflammation was found in the explant.

Both thin (2 mm) and thick (4 mm) soft tissue structures showed full depth host cell infiltration (FIGS. 11-13). New blood vessels were found in all implanted soft tissue structures. No inflammation or only mild neutrophil infiltration in soft tissue structures. There was no encapsulation shown in all soft tissue structure implants.

Example 6: Implantation of Sponge-Like Soft Tissue Structure in a Mouse Open Wound The implant samples and male athymic mice were prepared as Example 5.

An approximately 1 cm incision, one on each side of the dorsal midline was created. Two subcutaneous pockets approximately 0.15 cc were formed from these incisions using blunt dissection. The implant samples of the soft tissue structures were rehydrated with isotonic saline (50 µL) for a minimum of 5 minutes prior to implantation. The implants were inserted in the subcutaneous pocket with part of implant samples exposed to the air. Each animal was housed separately in a clean cage and monitored until the animal is alert and mobile.

After 4 weeks of implantation, animals were euthanized and histology slides were prepared as Example 5. Tissue sections were evaluated semi-quantitatively for fibroblast infiltration of the implant, degree of neovascularization, degree of re-epithelialization on exposed sponge, inflammatory cell response (macrophage/giant cells, neutrophils), and fibrous tissue/encapsulation.

Figure 14:
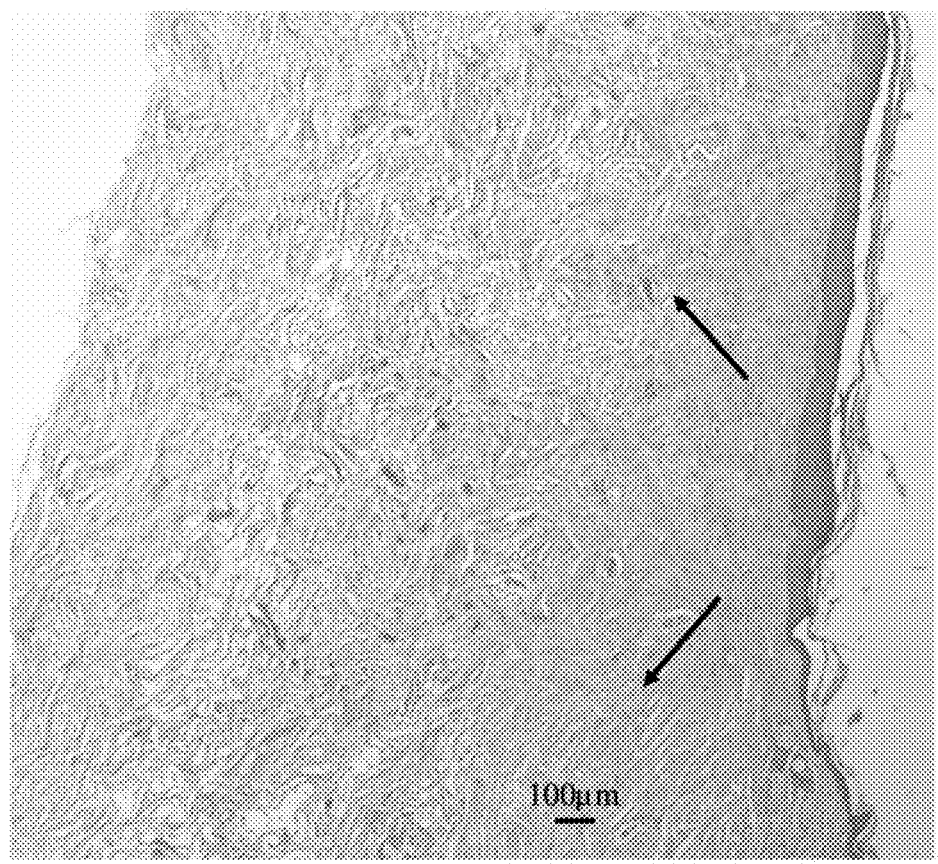
FIG. 14 depicts H&E staining of a porous soft tissue implant explanted after 4 weeks implantation in an athymic mouse open wound. Arrows showed the re-epithelialization of the soft tissue structure by mouse keratinocyte.

Both thin (2 mm) and thick (4 mm) soft tissue structures showed full depth host cell infiltration. New blood vessels were found in all implanted soft tissue structures. Exposed soft tissue structures were re-epithelialized with mouse skin keratinocytes (FIG. 14). Mild to moderate neutrophil infiltration was found in soft tissue structures due to the open wound without dressing. There was no encapsulation shown in all soft tissue structure implants.

Example 7: Preparation of Tissue Repair Implants with Placental Membrane

Human placenta was obtained from Caesarean section with donor consent and placed on wet ice. The placental membrane was cleaned and cut into small (about 20 cm by 2.0 cm) pieces (e.g., crude fragments). About 12 grams of placental membrane and three pieces of ice cubes were mechanically dispersed (e.g., blended) (Osterizer from Sunbeam-Oster, Inc.) together for 2 minutes, and three more pieces of ice cubes were added into the mixture and dispersed for another minute. Then the dispersed soft tissue was transferred onto a sterile sieve. The layer of fibrous soft tissue was transferred into molds (e.g. petri dishes or test tubes) and weighed. The undispersed tissue was mixed with two ice cubes and dispersed for another 2 minutes. Then the dispersed soft tissue was transferred onto a sterile sieve. The layer of dispersed soft tissue was transferred into molds and weighed. Repeat this process until majority of soft tissue was dispersed. The molds containing dispersed fibrous tissue were stored at −20° C. or −80° C. freezer for a minimum of 4 hours, followed by freeze drying for 48-96 hours.

Example 8: Preparation of Tissue Repair Implants with Human Dermis and DBM

Cleaned dermis was prepared as described in example 1 and cut into small (about 1.0 cm by 1.0 cm) pieces. About 12 grams of dermis and two pieces of ice cubes were mechanically dispersed (Osterizer from Sunbeam-Oster, Inc.) together for 2 minutes, and two more pieces of ice cubes were added into the mixture and dispersed for two minutes. Then the dispersed soft tissue was transferred into molds (e.g. petri dishes or test tubes) and weighed. Demineralized bone matrix particles were added into dispersed soft tissue and mixed well. Three different ratios of soft tissue to DBM weight were used.

The molds containing dispersed fibrous tissue and DBM mixture were stored at −20° C. or −80° C. freezer for a minimum of 4 hours, followed by freeze drying for 48-96 hours.

Example 9: Preparation of Tissue Repair Implants with Different Types of Soft Tissue The dispersed soft tissue is prepared as Example 1 and another batch of dispersed soft tissue prepared as Example 7. Both types of dispersed soft tissue are transferred into molds (e.g. petri dishes or test tubes) at different ratios (4:1, 2:1, 1:1, 1:2, and 1:4). The molds containing disposed soft tissue mixtures are stored at −20° C. or −80° C. freezer for a minimum of 4 hours, followed by freeze drying for 48-96 hours. The resultant porous soft tissue structures are then sent out for sterilization by gamma irradiation.

Example 10: Preparation of Sponge-Like Soft Tissue Structure Repair Implants with Ice, Room Temperature Water, or Cold Water Method 1: Cleaned and decellularized/devitalized dermis was prepared as described in example 1 and cut into small (about 1.0 cm by 1.0 cm) pieces. About 24 grams of dermis and ice cubes (3 pieces, each made with 10 mL of sterile ultraputure water) were mechanically dispersed (Osterizer from Sunbeam-Oster, Inc.) together for 2 minutes. Then the processed soft tissue was transferred onto a sterile sieve. The undispersed tissue pieces were picked out and mixed with three ice cubes and dispersed for another 2 minutes. The processed soft tissue was transferred again onto the same sterile sieve. The undispersed tissue pieces were picked out and mixed with two ice cubes and dispersed for another 2 minutes. The processed soft tissue was transferred onto the same sieve. The layer of dispersed soft tissue was transferred into molds and weighed. This was named as dermal sponge (ice).

Method 2: Another 24 grams of dermis (about 1.0 cm by 1.0 cm) pieces and 30 mL of room temperature sterile ultrapure water were mechanically dispersed (Osterizer from Sunbeam-Oster, Inc.) together for 2 minutes. Then the dispersed soft tissue was transferred onto a sterile sieve. The undispersed tissue was pick up and mixed with 30 mL of room temperature sterile ultrapure water and dispersed for another 2 minutes. The processed soft tissue was transferred again onto the same sterile sieve. The undispersed tissue pieces were picked out and mixed with 20 mL of room temperature sterile ultrapure water and dispersed for another 2 minutes. Then the dispersed soft tissue was transferred onto the sterile sieve. The layer of dispersed soft tissue was transferred into molds and weighed. This was named as dermal sponge (RT H2O).

Method 3: Another 24 grams of dermis (about 1.0 cm by 1.0 cm) pieces and 30 mL of cold sterile ultrapure water (from 4° C. refrigerator) were mechanically dispersed (Osterizer from Sunbeam-Oster, Inc.) together for 2 minutes. Then the processed soft tissue was transferred onto a sterile sieve. The undispersed tissue was pick up and mixed with 30 mL of cold sterile ultrapure water (from 4° C. refrigerator) and dispersed for another 2 minutes. The processed soft tissue was transferred again onto the same sterile sieve. The undispersed tissue pieces were picked out and mixed with 20 mL of cold sterile ultrapure water and dispersed for another 2 minutes. Then the dispersed soft tissue was transferred onto the sterile sieve. The layer of dispersed soft tissue was transferred into molds and weighed. This was named as dermal sponge (cold H2O).

The molds containing dispersed soft tissue (method 1 method 2, or method 3) were freeze dried for 48-96 hours at a controlled freezing rate of about 3-5° C. per minute. Half of made soft tissue sponges were sent for terminal sterilization with gamma-irradiation at 16-18 kGy on dry ice.

Example 11: Mercury Porosimetry for Dermal Sponge-Like Soft Tissue Structure Made with Three Different Methods Samples of 8 mm biopsy punches from cleaned and decellularized/devitalized dermis as described in Example 1, the dermal sponges made with the three methods as described in Example 10: dermal sponge (ice), dermal sponge (cold H2O), and dermal sponge (RT H2O), were used for porosity measurement using mercury porosimetry analysis.

Figure 17:
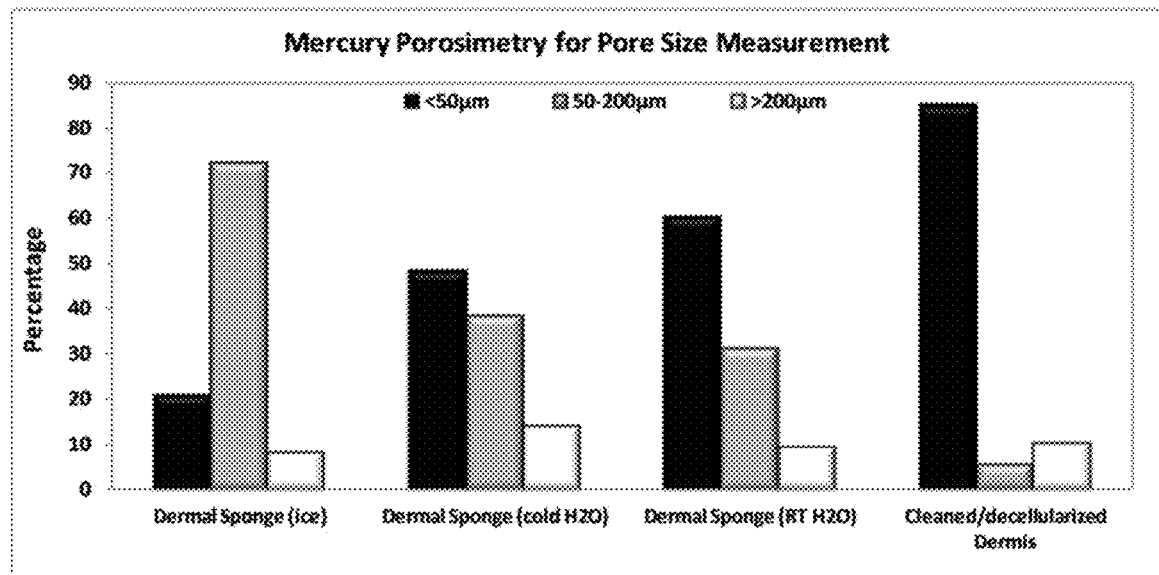
FIG. 17 depicts percentage of pores in different pore size ranges as measured with mercury porosimetry for cleaned/decellularized dermis, porous soft tissue scaffold made with dermis and ice, porous soft tissue scaffold made with dermis and cold water, and porous soft tissue scaffold made with dermis and room temperature water.

The results showed that more than 80% of the pores in cleaned and decellularized/devitalized dermis were smaller than 50 micron and less than 6% of the pores were between 50-200 micron (FIG. 17). More than 70% of the pores in dermal sponge (ice) were between 50-200 micron and about 20% of the pores were smaller than 50 micron. About 30-40% of the pores in dermal sponge (cold H2O and RT H2O) were 50-200 micron and about 48-60% of the pores were smaller than 50 micron.

Figure 18:
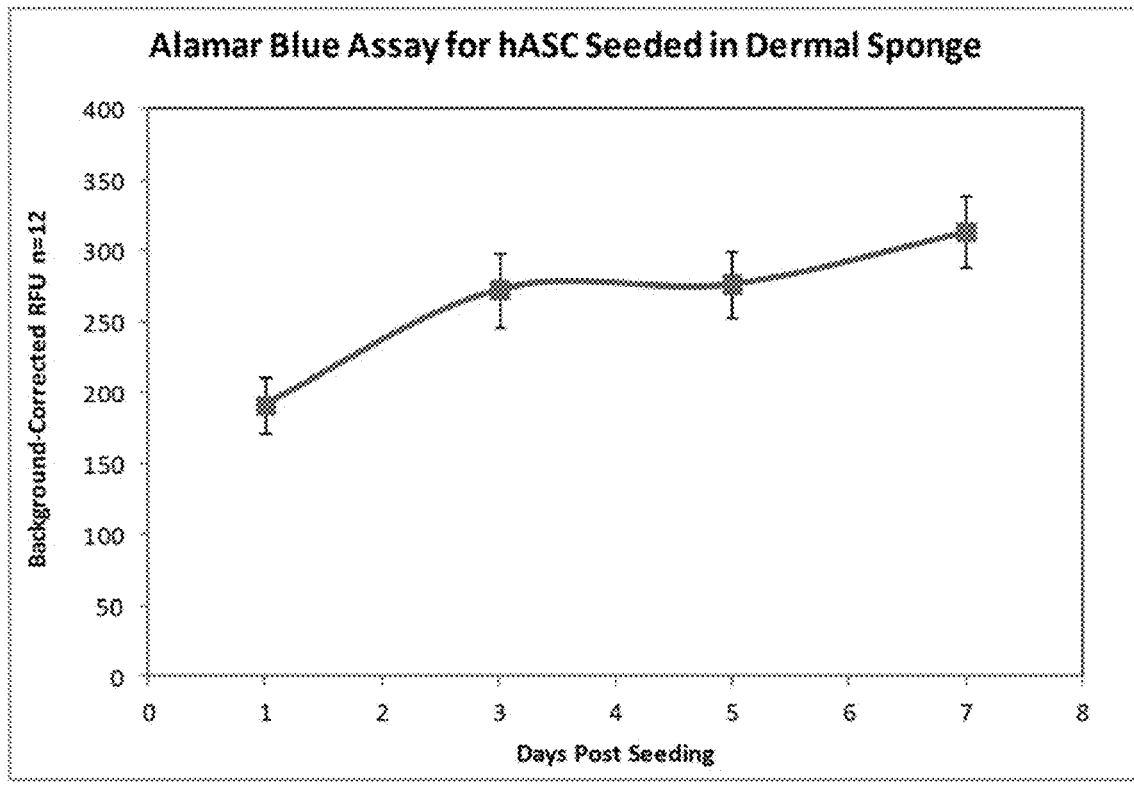
FIG. 18 depicts human adipose derived stem cell growth in porous soft tissue scaffold made with dermis over 7 days of culture.

Example 12: In Vitro Human Adipose Derived Stem Cell (hASC) Attachment, Proliferation, and Differentiation in Sponge-Like Soft Tissue Structure Discs were made from dermal sponge prepared as example 11, method 1 using 6 mm biopsy punches. The height of these dermal sponge discs were about 4 mm. They were pre-soaked in MSC medium (LifeLine Cell Technology) at 37° C. for 2 hours before seeding. Human adipose derived stem cells at 3rd passage were seeded into the prepared dermal sponge discs (200,000 cells/disc) and cultured for 7 days in MSC media in a 12-well plate pre-coated with 1.2% poly (2-hydroxyethyl methacrylate) to prevent cell attachment to the culture plate. The culture media was changed to AlamarBlue reagent (10%) in MSC media on day 1, day 3, day 5, and day 7 and incubated for 2 hours. The fluorescent intensity of the culture media with AlamarBlue reagent was measured. The intensity of the fluorescence is correspondent to the viability/metabolism of the cells, i.e., the higher the intensity the more viable/metabolic active cells. As shown in FIG. 18, the dermal sponge not only maintained the cell viability but also support cell growth as the cell number in the dermal sponge increased steadily over 7 days of culture.

Figure 19:
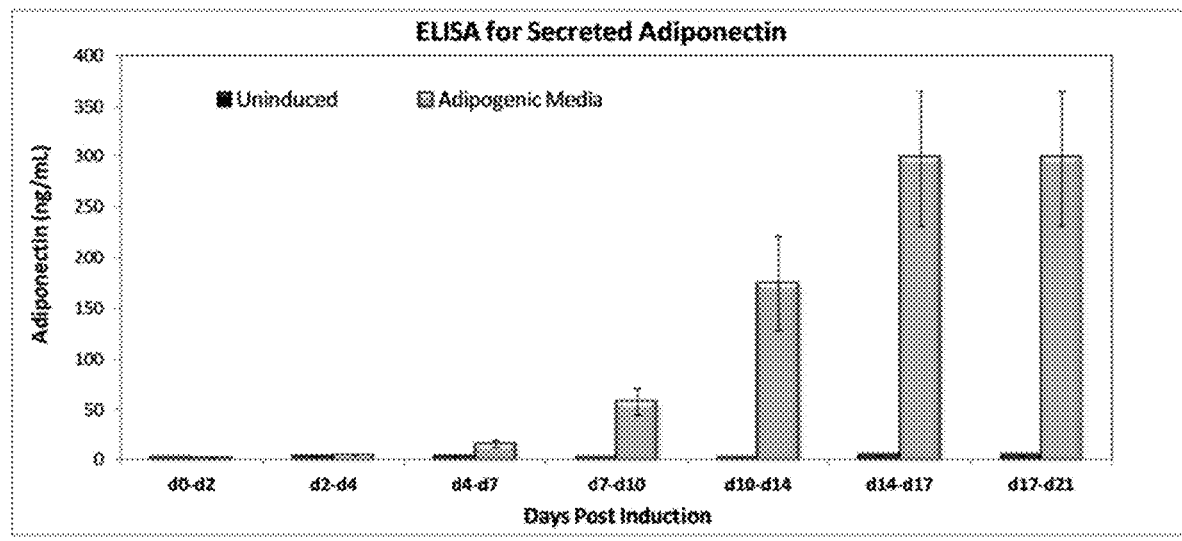
FIG. 19 depicts secreted adiponectin in culture media from differentiated adipocytes in porous soft tissue scaffold made with dermis over three weeks of culture with or without adipogenic media.

Followed the 7-day culture in MSC media, the media in half of samples (6 wells) was changed to AdipoLife DfKt-1 adipogenic medium (LifeLine Cell Technology) and cultured for 3 weeks with the media change every 2-3 days. For each media change, the spent media were collected and stored at −80° C. freezer for ELISA analysis of adiponectin, an adipogenic marker, using Acrp30 Quantikine ELISA Kit (R&D Systems, Inc.). The adiponectin ELISA showed that dermal sponge supported hASC differentiation to adipocytes under adipogenic media culture condition as compared to the samples without adipogenic media (FIG. 19).

Figure 20:
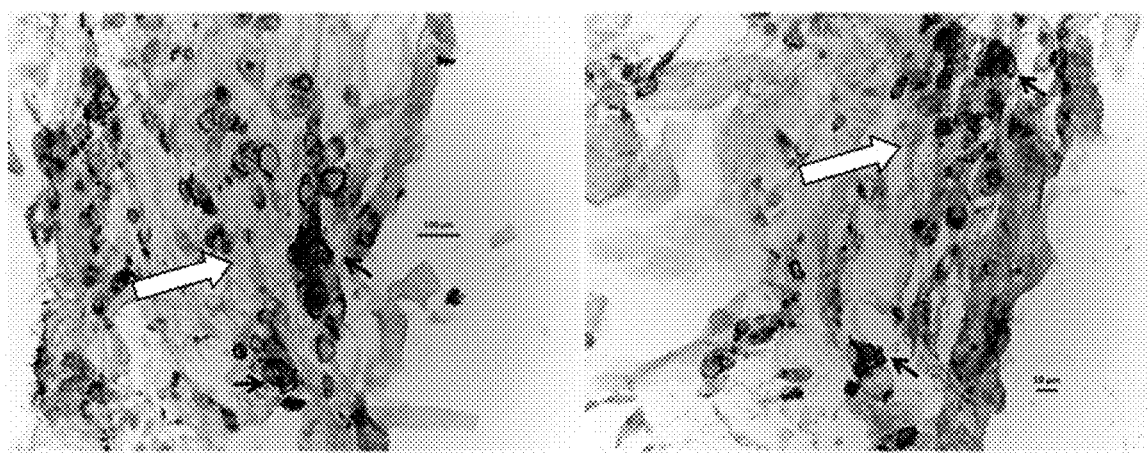
FIG. 20 depicts perilipin staining (brown color pointed by arrows) in differentiated adipocytes in porous soft tissue scaffold made with dermis after two weeks of culture with adipogenic media.

After 2 week and 3 week culture in adipogenic media, hASC seeded dermal sponge samples were also taken for histological preparation and immunohistological staining for perilipin, a highly phosphorylated adipocyte proteins that are localized at the surface of the lipid droplet, using anti-parilipin A (Abcam ab3526). The secondary antibody was biotinylated goat anti-rabbit IgG, followed by streptavidin peroxidase-conjugate treatment and AEC substrate development. The perilipin positive stained cells (open arrows) were found in sections made from hASC seeded sponge after 2 week adipogenic media culture (FIG. 20).

Example 13: Long Term Subcutaneous Implantation of Sponge-Like Soft Tissue Structure Using a Mouse Model Implant samples were generated by taking 8 mm biopsy punches from freeze dried dermal sponge prepared as Example 10. Biopsy punches (8 mm) from the cleaned and decellularized/devitalized dermis prepared as Example 1 were used as an implantation control. Half of cleaned/decellularized dermis and dermal sponges punches were terminal sterilized with gamma-irradiation of 16-18 kGy on dry ice. Biopsy punches (8 mm) from HELISTAT®, an absorbable collagen hemostatic sponge, were used as another implantation control.

Male athymic mice (Nu/Nu Foxn1nu), about 6 weeks in age, were acquired from Charles Rivers Laboratories and went through a minimum 72-hr acclamation period prior to surgery. Animals were housed in an ultra barrier facility in sterile cages with sterile bedding and food. The animals were weighed to the nearest 0.1 g and anesthesia was induced by isoflurane (1 to 5% in O2 to effect) and maintained at 2 to 3% in O2 for the surgery. Each animal received peri-operative analgesic Buprenorphine at 0.1 to 1.0 mg/kg via subcutaneous injection and ophthalmic ointment was placed over the eyes. The upper back near the shoulder area was swabbed twice with betadine and alcohol. An approximately 1 cm incision, one on each side (para-medial) of the back of the animal near its shoulder area was created. Two subcutaneous pockets were formed from these incisions using blunt dissection.

Cleaned and decellularized/devitalized dermis controls were soaked in isotonic saline for a minimum of 5 minutes prior to implantation. Dermal sponges and Helistat control samples were rehydrated with isotonic saline (100 μL) for a minimum of 5 minutes prior to implantation. The implants were inserted in the subcutaneous pocket. Each animal received a total of 2 implants. Incisions were closed with interrupted sutures.

Animals were monitored twice daily for the first 48 hours followed by once per week until termination of study. Sutures were removed at 10-14 days post-op. Photos of implant sites were taken right after implantation and every 2-3 weeks until explantation. At the designated time point (6-week, 12-week, and 24-week), animals were euthanized by CO2 inhalation and their weights were recorded.

Following euthanasia the implant sites were carefully exposed by cutting the skin and subcutaneous tissues about 5 mm away from the implant. Any gross evidence of inflammation, infection, fibrosis, hematoma, or seroma were noted and photographed. The implanted sample and the 3-5 mm of surrounding tissue was excised and fixed in 10% neutral buffered formalin (NBF) at ambient temperature for a minimum of 4 days to achieve complete fixation.

Each explant sample was cut along its longest midline to create two halves. The resulting specimens were embedded together (cut face down) in the same paraffin block. Sections at 5 micron thickness were made and stained with hematoxylin and eosin (H&E) or Masson's Trichrome staining. The section with the largest cross section of implant material was used for evaluation. Cross sectional area of the implant material and adipose tissue was measured separately using Image-J software.

Figure 22:
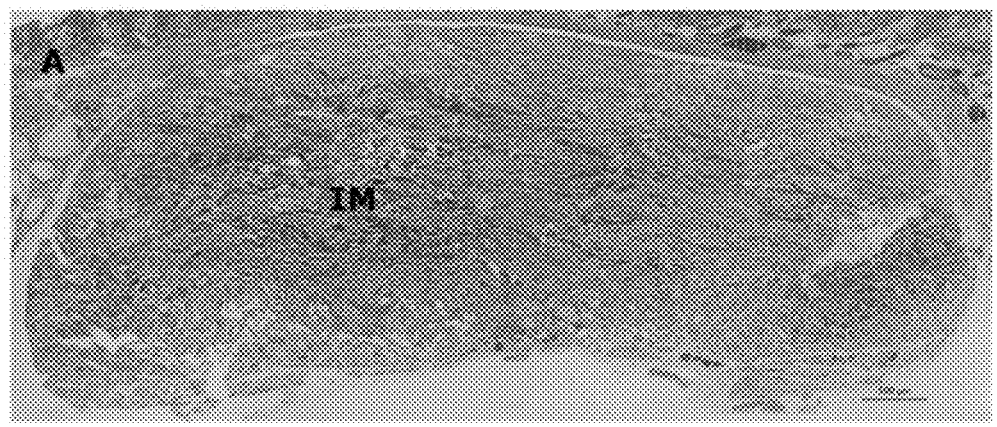
FIG. 22 depicts the cross section of the cleaned/decellularized dermis (A) and the porous soft tissue scaffolds made from dermis (B) stained with Masson's trichrome method after 24 weeks of implantation in mouse subcutaneous model. IM indicates the implant sample.
Figure 22:
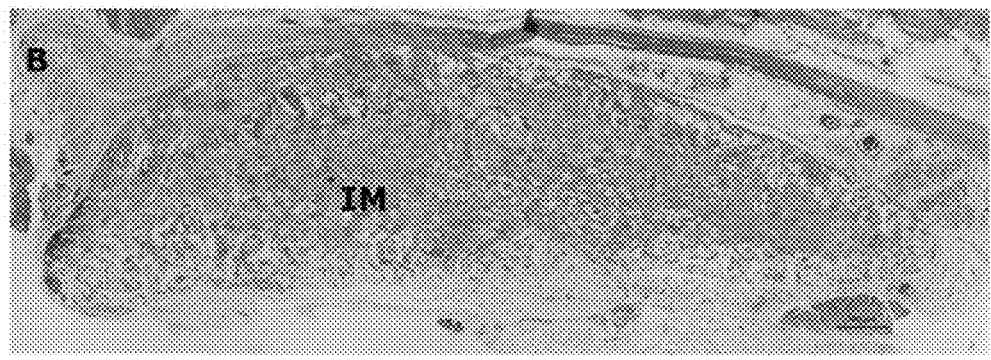
Figure 23:
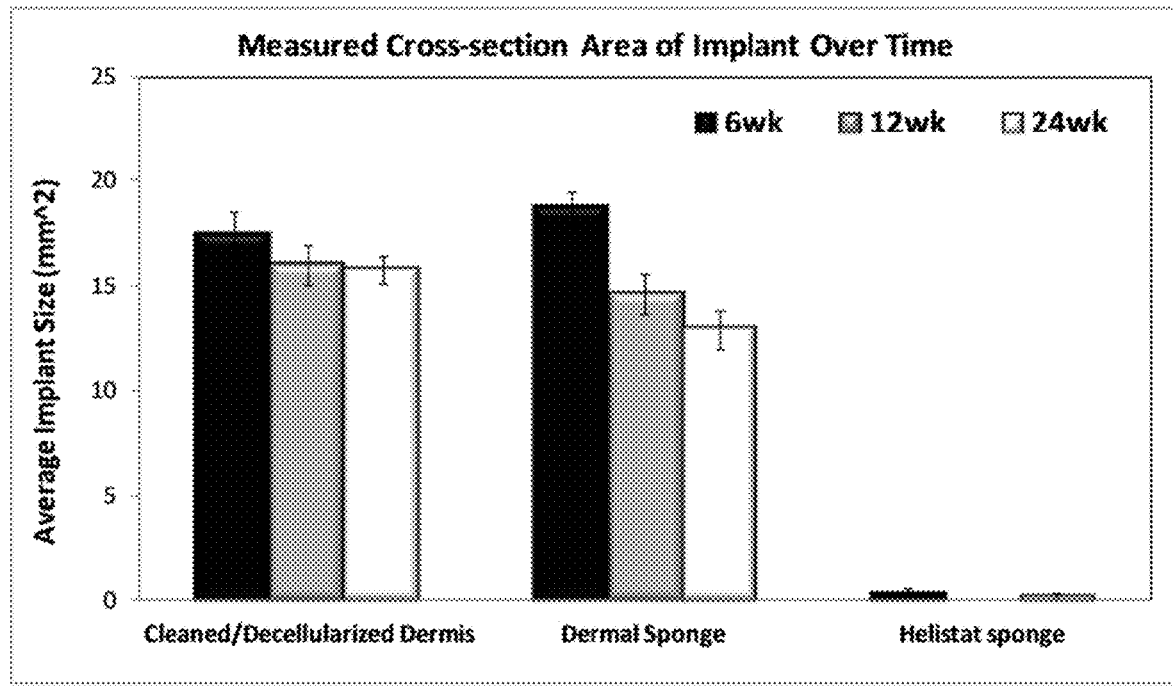
FIG. 23 depicts the measured cross section area of the cleaned/decellularized dermis, the porous soft tissue scaffolds made from dermis, and Helistat sponge over the implantation time of 6 weeks, 12 weeks, and 24 weeks.
Figure 24:
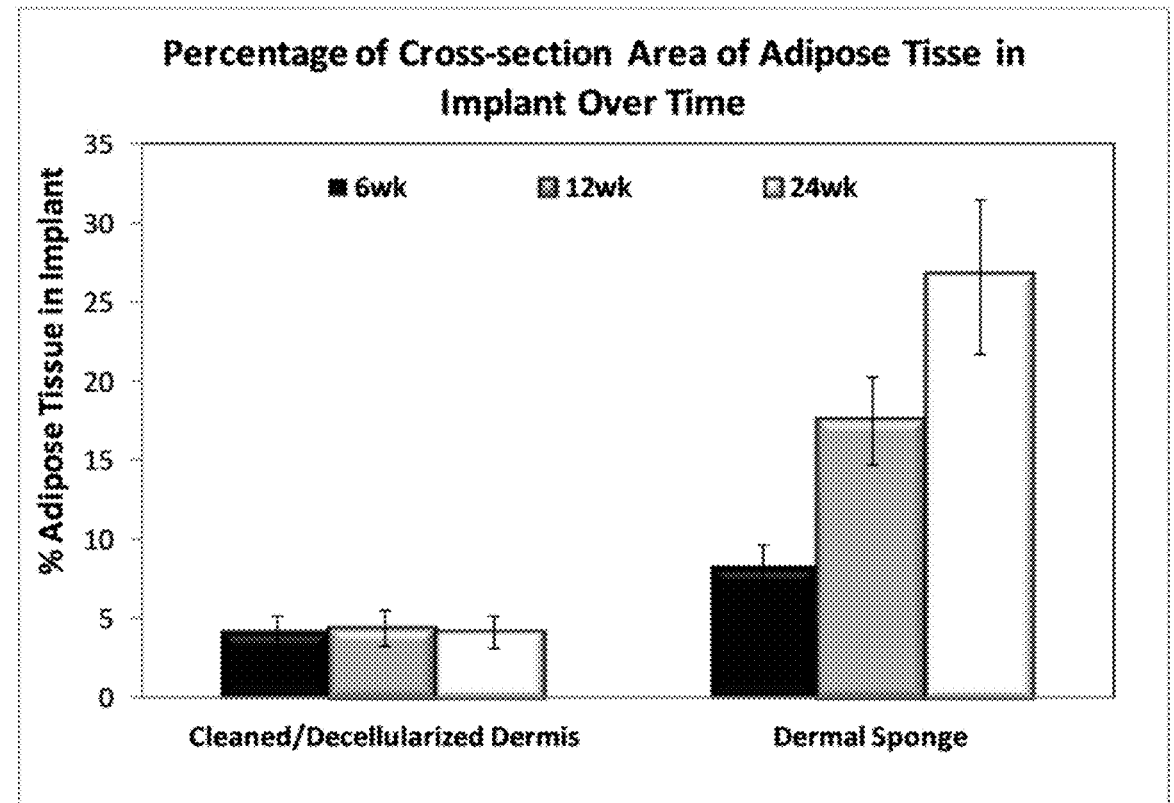
FIG. 24 depicts the percentage of the adipose tissue in the measured cross section area of implants from the cleaned/decellularized dermis and the porous soft tissue scaffolds made from dermis over the implantation time of 6 weeks, 12 weeks, and 24 weeks.

The images of the cross-section of the cleaned/decellularized dermis (FIG. 22A) and dermal sponge (FIG. 22B) with the Masson's trichrome staining showed cell infiltration, angiogenesis, and adipose tissue inside of implant material. The measured cross-section area of gamma-irradiated implant samples were compared among cleaned/decellularized dermis, dermal sponge, and Helistat control for three time points: 6 week, 12 week, and 24 week (FIG. 23). From 6 week to 24 week, the implant cross-section area of dermal sponge decreased about 30%, while the implant cross-section area of cleaned/decellarized dermis decreased about 10%. But the implant of Helistat was most absorbed after 6 week implantation. At 24 week the adipose tissue cross-section area of dermal sponge was more than twice as much as the 6 week explant, while the adipose tissue cross-section area of cleaned/decellarized dermis maintained about the same from 6 week to 24 week explants (FIG. 24).

Figure 25:
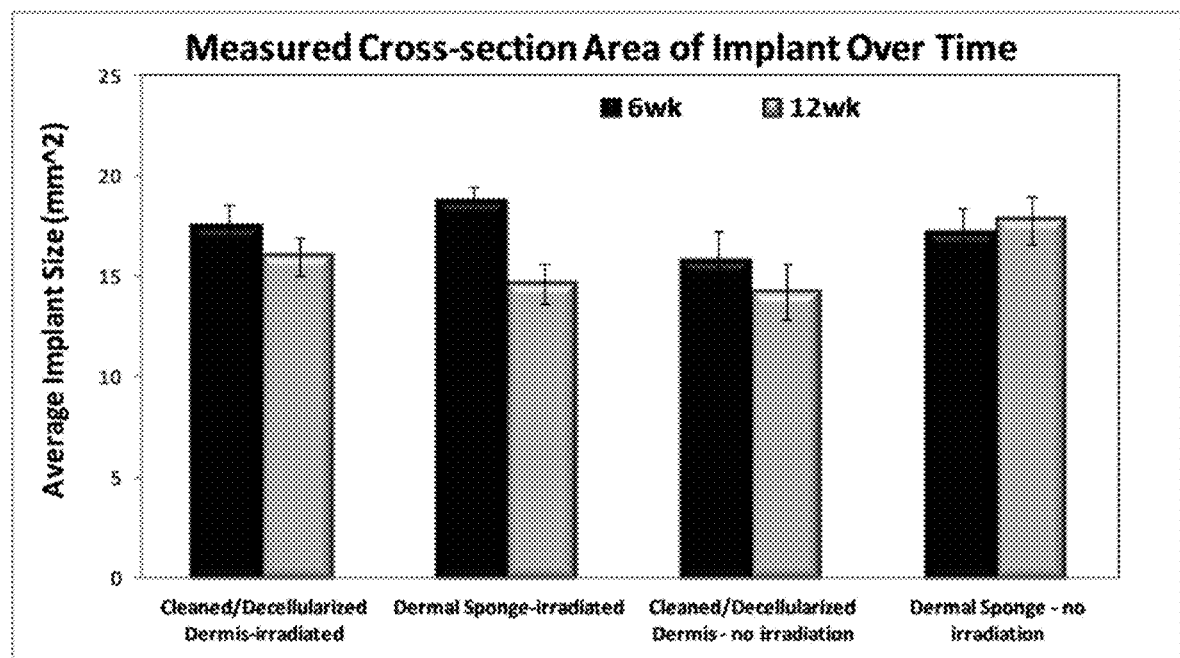
FIG. 25 depicts the measured cross section area of the cleaned/decellularized dermis and the porous soft tissue scaffolds made from dermis with and without gamma-irradiation over the implantation time of 6 weeks and 12 weeks.

The measured cross-section area of implant samples from cleaned/decellularized dermis and dermal sponge was compared between with gamma-irradiation and without gamma-irradiation (FIG. 25). From 6 week to 12 week, the implant cross-section area of irradiated dermal sponge decreased about 22%, while the implant cross-section area of non-irradiated dermal sponge maintained about the same.

Example 14: Preparation of Sponge-Like Soft Tissue Structure with Placenta and Placental Membrane Human term placenta including placental membrane recovered from cesarean section of one authorized research donor was used to make placenta sponges. Within 4 hours of placenta recovery, the placental membrane was cut around the skirt of placenta and separated from the placenta. The remaining placenta was cut to small pieces (1-2 cm×1-2 cm×1-2 cm), and rinse 5 times with isotonic solution (DPBS). Red blood cell (RBC) lysis buffer was used to remove RBC from placenta tissue and placental membrane, followed by saline rinses.

About 24 grams of cleaned placenta tissue and ice cubes (2 pieces, each made with 10 mL of sterile ultraputure water) were mechanically dispersed (Osterizer from Sunbeam-Oster, Inc.) together for 2 minutes. The dispersed soft tissue was transferred into molds and weighed. This was named as placenta sponge. About 24 grams of cleaned placental membrane and ice cubes (2 pieces, each made with 10 mL of sterile ultraputure water) were mechanically dispersed (Osterizer from Sunbeam-Oster, Inc.) together for 0.5 minute. The layer of dispersed soft tissue was transferred into molds and weighed. This was named as placental membrane sponge. After all samples were prepared, molds with the dispersed tissue were freeze dried at control freeze rate of 3.5° C. per minute.

Example 15: Subcutaneous Implantation of Sponge-Like Soft Tissue Structure Made with Placenta and Placental Membrane Implant samples were generated by taking 8 mm biopsy punches from freeze dried placenta sponge and placental membrane sponge prepared as Example 14. Male athymic mice (Nu/Nu Foxn1nu) were prepared as described in Example 13. Placenta sponge and placental membrane sponges were rehydrated with isotonic saline (100 µL) for a minimum of 5 minutes prior to implantation. The implants were inserted in the subcutaneous pocket. Each animal received a total of 2 implants. Incisions were closed with interrupted sutures.

Animals were monitored twice daily for the first 48 hours followed by once per week until termination of study. Sutures were removed at 10-14 days post-op. Photos of implant sites were taken right after implantation and every 2-3 weeks until explantation. At the designated time point (4-week and 6-week), animals were euthanized by CO2 inhalation and their weights were recorded.

Following euthanasia the implant sites were carefully exposed by cutting the skin and subcutaneous tissues about 5 mm away from the implant. Any gross evidence of inflammation, infection, fibrosis, hematoma, or seroma were noted and photographed. The implanted sample and the 3-5 mm of surrounding tissue was excised and fixed in 10% neutral buffered formalin (NBF) at ambient temperature for a minimum of 4 days to achieve complete fixation.

Each explant sample was cut along its longest midline to create two halves. The resulting specimens were embedded together (cut face down) in the same paraffin block. Sections at 5 micron thickness were made and stained with hematoxylin and eosin (H&E) or Masson's Trichrome staining. Some sections have also stained for perilipin in adipocytes using anti-parilipin A (Abcam ab3526). The secondary antibody was biotinylated goat anti-rabbit IgG, followed by streptavidin peroxidase-conjugate treatment and AEC substrate development. The section with the largest cross section of implant material was used for evaluation. Cross sectional area of the implant material and adipose tissue was measured separately using Image-J software.

Figure 26A:
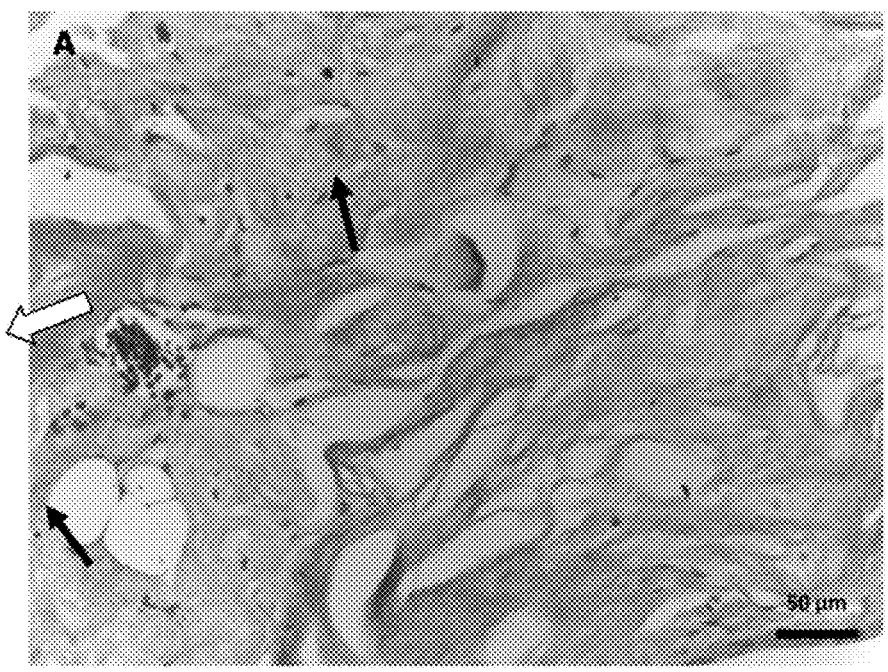
FIGS. 26A-C depict Masson's trichrome staining of the porous soft tissue implant made with placenta (A) and placental membrane (B): cell infiltration (black arrows), and angiogenesis (open arrows). The adipocytes and adipose tissue was stained in red color with immunohistochemistry staining of perilipin (black arrows in FIG. 26C) in the porous soft tissue implant made with placental membrane after 4 weeks subcutaneous implantation in an athymic mouse.
Figure 26B:
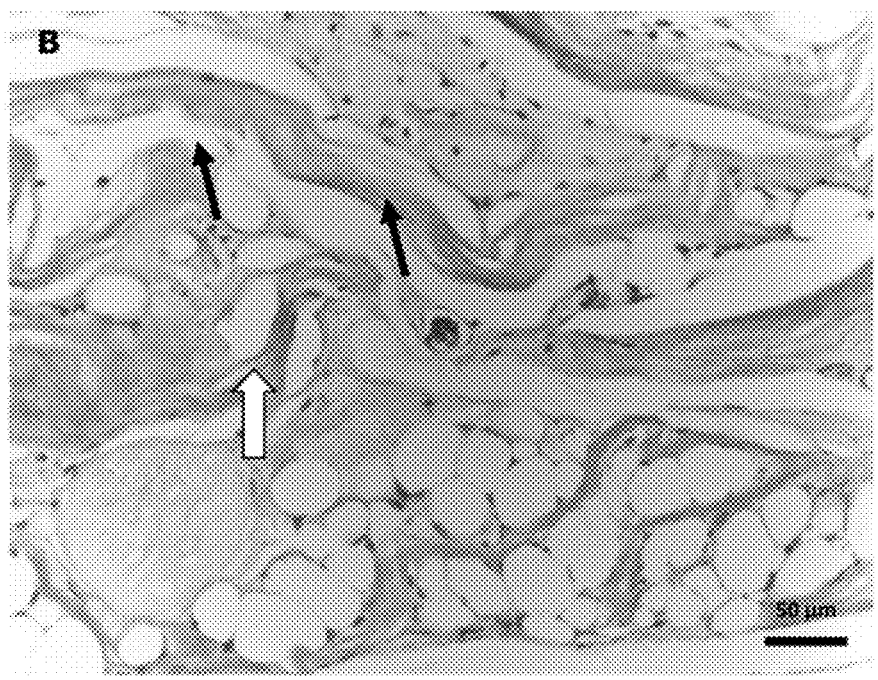
Figure 26C:
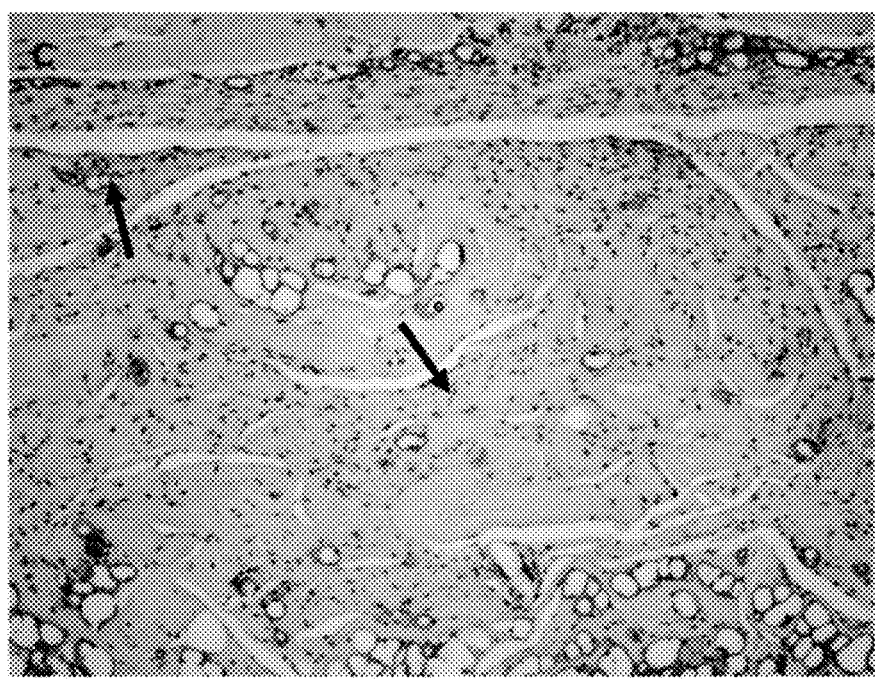
Figure 27:
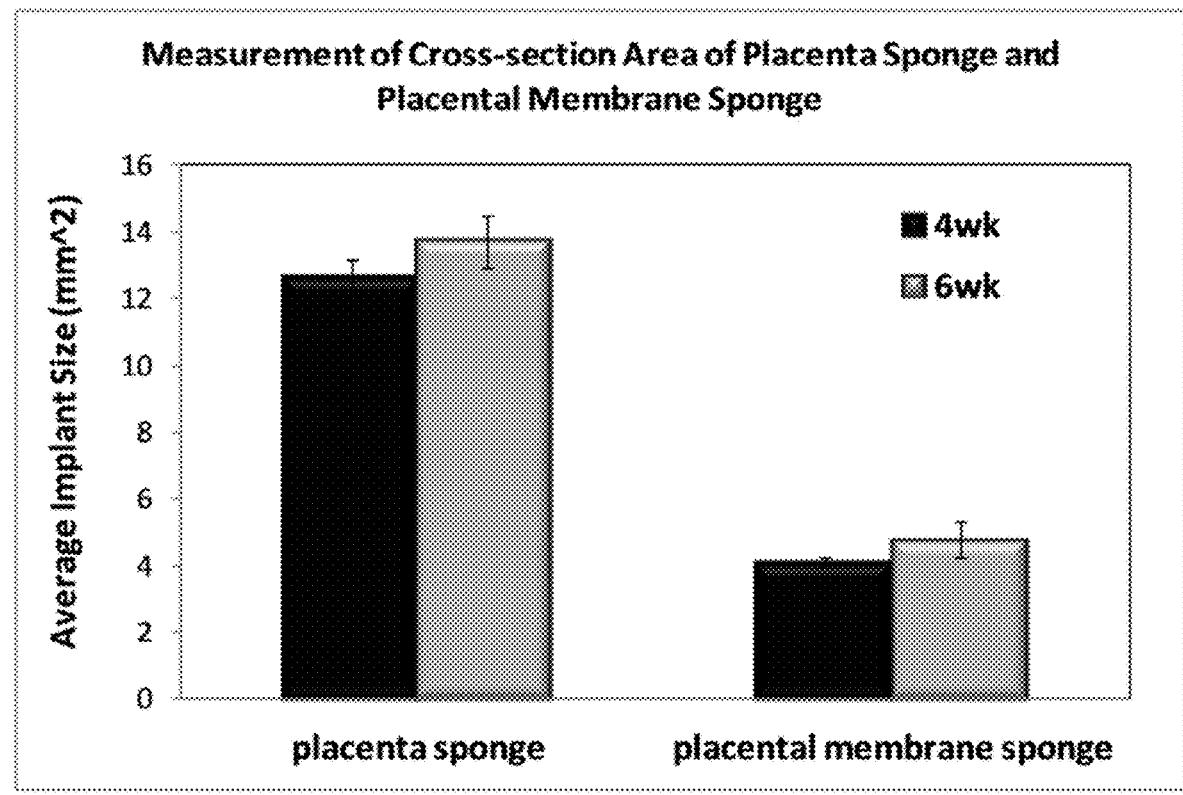
FIG. 27 depicts the measured cross section area of the porous soft tissue implant made with placenta and placental membrane over the implantation time of 4 weeks and 6 weeks.

The images of the cross-section of the placenta sponge (FIG. 26A) and placental membrane sponge (FIG. 26B) with the Masson's trichrome staining showed cell infiltration (black arrows), angiogenesis (open arrows), and adipose tissue inside of implant material. The adipocytes and adipose tissue was stained in red color with immunohistochemistry staining of perilipin (black arrows in FIG. 26C). There was no significant difference in implant cross-section area between 4 week and 6 week for both placenta sponge and placental membrane sponge (FIG. 27).

Example 16: Preparation of Sponge-Like Soft Tissue Structure with Human Fascia

Human fascia recovered from authorized research donors was used to make sponge-like soft tissue structure. Fascia pieces were cleaned of any extra tissue and blood with solution containing detergents and either freeze dried or kept frozen until use. The freeze dried fascia pieces were hydrated in ultrapure water for 2 days at room temperature prior to use. All fascia were cut to 1-2 cm×1-2 cm pieces and weighed. About 12 grams of freeze dried or freeze/thawed fascia and ice cubes (2 pieces, each made with 10 mL of sterile ultraputure water) were mechanically dispersed (Osterizer from Sunbeam-Oster, Inc.) together for 2 minutes. Then the processed soft tissue was transferred onto a sterile sieve. The un-dispersed tissue pieces were picked out and mixed with two ice cubes and dispersed for another 2 minutes. The processed soft tissue was transferred again onto the same sterile sieve. The layer of dispersed soft tissue was transferred into molds and weighed. This was named as fascia sponge (freeze/thawed) group. In addition, about 14 grams of dispersed soft tissue was mixed with 1.44 grams of demineralized bone matrix. This was named as fascia/DBM group. For the freeze-dried fascia, more un-dispersed tissue pieces were picked out after two runs and mixed with one more ice cube and dispersed for another 1 minute. The processed soft tissue was transferred onto the same sieve. The layer of dispersed soft tissue was transferred into molds and weighed. This was named fascia sponge (freeze-dried) group.

Figure 28:
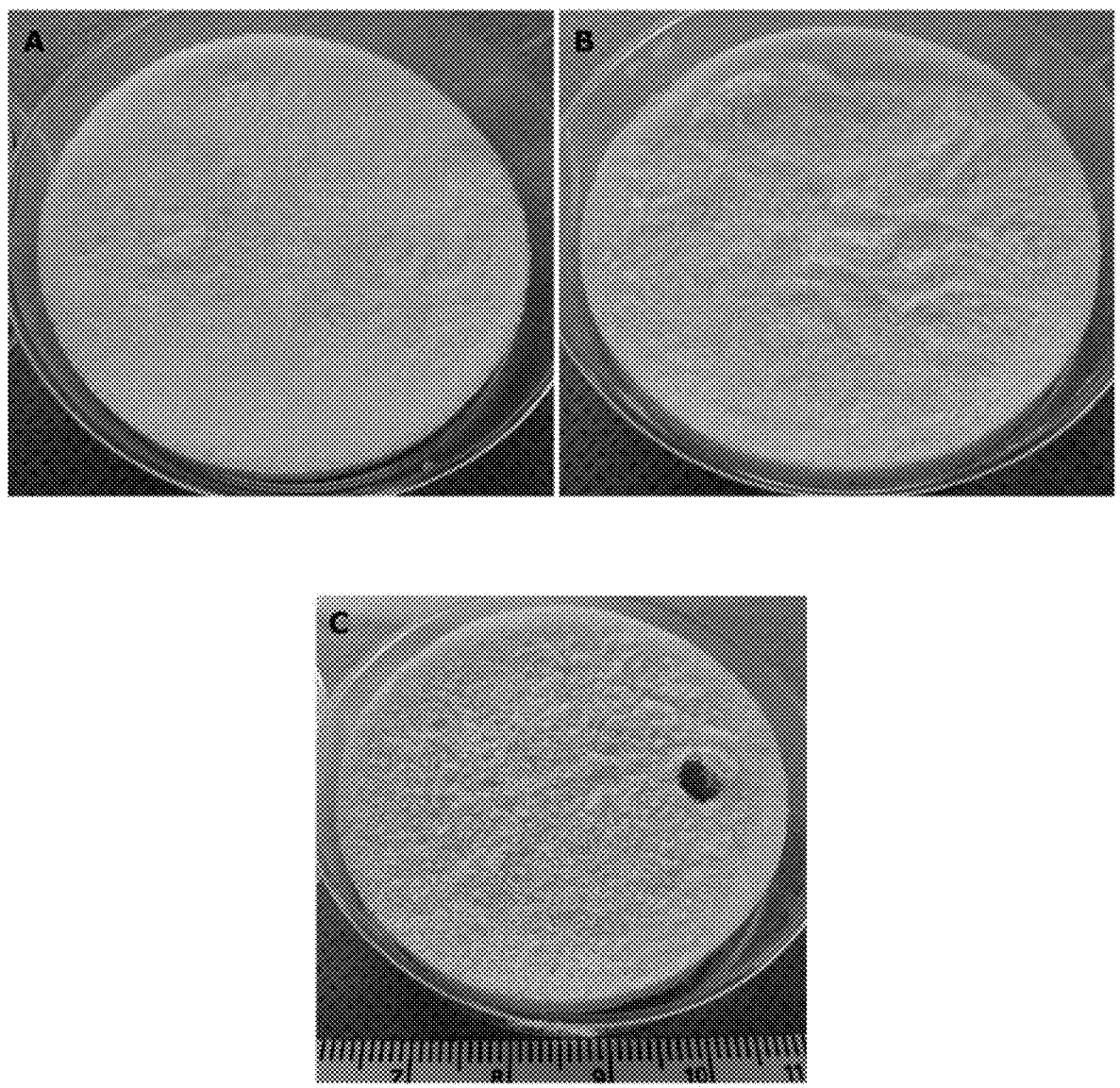
FIG. 28 depicts the exemplary porous soft tissue scaffolds made from freeze-dried human fascia (A), freeze/thawed human fascia (B), and freeze/thawed human fascia mixed with DBM (C).
Figure 29:
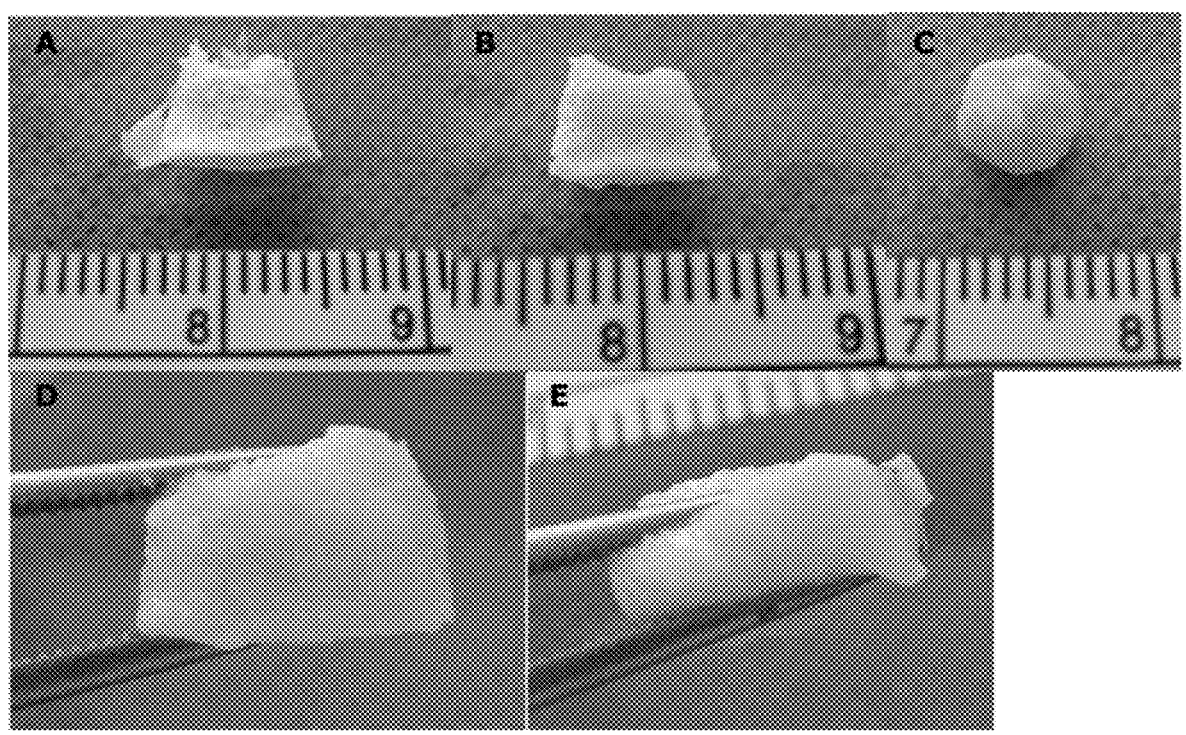
FIG. 29 depicts the exemplary porous soft tissue scaffolds made from freeze/thawed human fascia mixed with DBM at dry state (A), after hydration with isotonic saline (B), and molded to a ball shape (C). The hydrated fascia/DBM sponge was picked up with a pair of forceps (D) and pressed with forceps (E).

After all samples were prepared, molds containing the dispersed tissue were freeze dried. The representative pictures were taken for the fascia sponge (freeze-dried) group (FIG. 28A), the fascia sponge (freeze/thawed) group (FIG. 28B), and the fascia/DBM group (FIG. 28C). Part of fascia/DBM sponge was cut (FIG. 29A) and hydrated with isotonic saline (FIG. 29B), and molded to a ball shape (FIG. 29C). The hydrated fascia/DBM sponge was also picked up with a pair of forceps (FIG. 29D) and pressed with forceps (FIG. 29E).

The invention claimed is:

1. A biologically functional scaffold comprising one or more dispersed soft tissue(s) prepared from one or more native soft tissue(s), wherein (i) the dispersed soft tissue(s) comprise randomly interwoven collagen fibers and/or collagen fiber bundles, (ii) the density of the biologically functional scaffold is from about 0.005 g/cm$^3$ to 0.5 g/cm$^3$ in a dry state, and (iii) the biological functional scaffold has a porous structure wherein a porosity of the biological functional scaffold is greater than a porosity of the one or more native soft tissue(s);
wherein a relative ratio of extracellular matrix macromolecule components in the dispersed soft tissue(s) is about the same as a relative ratio of extracellular matrix macromolecule components in the native soft tissue(s).

2. The biologically functional scaffold according to claim 1, wherein the biologically functional scaffold is produced by a method comprising dispersing one or more soft tissue(s), and extracellular matrix macromolecule components of the resulting biologically functional scaffold are not modified by the method of producing said scaffold.

3. The biologically functional scaffold according to claim 1, wherein the weight percentage of said one or more dispersed soft tissue(s) in said biologically functional scaffold is from 50% to 100% in the dry state.

4. The biologically functional scaffold according to claim 1, wherein the biologically functional scaffold comprises pores having an average diameter from 1 μm to 4000 μm.

5. The biologically functional scaffold according to claim 1, wherein an average void volume of the biologically functional scaffold is from about 10% to about 95%.

6. The biologically functional scaffold according to claim 1, wherein the biologically functional scaffold comprises fibers having an average diameter from 0.1 μm to 100 μm.

7. The biologically functional scaffold according to claim 1, wherein the biologically functional scaffold comprises fibers having an average length from 5 μm to 50 cm.

8. The biologically functional scaffold according to claim 1, wherein the one or more soft tissue(s) is selected from the group consisting of fascia, cartilage, tendon, ligament, pericardium, fat, muscle, urethra, small intestine, placenta, umbilical cord, and dermis.

9. The biologically functional scaffold according to claim 1, wherein the biologically functional scaffold is sterile.

10. The biological functional scaffold according to claim 1, wherein the biologically functional scaffold remains coherent after rehydration in a liquid, and wherein the largest cross-section area of the biologically functional scaffold is reduced less than 70% from 4 weeks to 24 weeks after implantation at an implant site in an animal.

11. The biological functional scaffold according to claim 1, wherein said soft tissue comprises dermis, fascia, tendon, placenta, and/or ligament, and wherein the density of the biologically functional scaffold is from about 0.05 g/cm3 to 0.5 g/cm3 in a dry state.

12. The biological functional scaffold according to claim 1, wherein said soft tissue comprises placental membrane, amniotic membrane, chorionic membrane, and/or umbilical cord, and wherein the density of the biologically functional scaffold is from about 0.005 g/cm3 to 0.2 g/cm3 in a dry state.

13. The biological functional scaffold according to claim 1, wherein the dispersed soft tissue is freeze-dried.

14. The biological functional scaffold according to claim 13, wherein the dispersed soft tissue is a porous soft tissue.

15. The biological functional scaffold according to claim 14, wherein the porous soft tissue has more space among the extracellular materials as compared with an undispersed soft tissue.

16. The biological functional scaffold according to claim 14, wherein the porous soft tissue has an increased void volume as compared with an undispersed soft tissue.

17. The biological functional scaffold according to claim 1, wherein the dispersed soft tissue is a porous soft tissue.

18. The biological functional scaffold according to claim 17, wherein the porous soft tissue has more space among the extracellular materials as compared with an undispersed soft tissue.

19. The biological functional scaffold according to claim 17, wherein the porous soft tissue has an increased void volume as compared with an undispersed soft tissue.

20. The biological functional scaffold according to claim 1, wherein the dispersed soft tissue is a freeze-dried porous soft tissue and has more space among the extracellular materials and an increased void volume as compared with an undispersed soft tissue.

21. The biological functional scaffold according to claim 1, wherein the dispersed soft tissue is decellularized or devitalized.

22. The biological functional scaffold according to claim 1, wherein the dispersed soft tissue does not comprise a non-naturally occurring crosslinker.

23. The biological functional scaffold according to claim 1, wherein the biological functional scaffold has a porous structure with over 30% of the pores larger than 50 μm.

* * * * *